United States Patent
Chaves et al.

(10) Patent No.: US 7,560,583 B2
(45) Date of Patent: Jul. 14, 2009

(54) MERCAPTOFUNCTIONAL SILANE AND PROCESS FOR ITS PREPARATION

(75) Inventors: Antonio Chaves, Chappaqua, NY (US); Eric Raymond Pohl, Mount Kisco, NY (US); Richard W. Cruse, Yorktown Heights, NY (US)

(73) Assignee: Momentive Performance Materials Inc., Albany, NY (US)

( * ) Notice: Subject to any disclaimer, the term of this patent is extended or adjusted under 35 U.S.C. 154(b) by 99 days.

(21) Appl. No.: 11/544,132

(22) Filed: Oct. 6, 2006

(65) Prior Publication Data
US 2008/0083350 A1   Apr. 10, 2008

(51) Int. Cl.
*C07F 7/08* (2006.01)
*C07F 7/10* (2006.01)
*C07F 7/12* (2006.01)

(52) U.S. Cl. ............... 556/429; 556/406; 556/413; 556/427

(58) Field of Classification Search ............ 556/429, 556/427, 406, 413
See application file for complete search history.

(56) References Cited

U.S. PATENT DOCUMENTS

| 5,116,886 | A | 5/1992 | Wolff et al. |
|---|---|---|---|
| 6,005,027 | A | 12/1999 | Guillet et al. |
| 6,548,594 | B2 | 4/2003 | Luginsland et al. |
| 6,849,754 | B2 | 2/2005 | Deschler et al. |
| 2006/0229399 | A1 | 10/2006 | Panzer et al. |
| 2008/0085960 | A1 | 4/2008 | Chaves et al. |

FOREIGN PATENT DOCUMENTS

| EP | 0 940 446 | 9/1999 |
|---|---|---|
| EP | 631982 | 9/2002 |

OTHER PUBLICATIONS

Joshi Prashant G: "Low Voc Silanes for Silica Tires" May 18, 2005, Technical Papers- American Chemical Society, Rubber Division, XX, XX, pp. 1-9, XP009072692.
U.S. Appl. No. 11/104,103, filed Apr. 12, 2005.
U.S. Appl. No. 11/358,369, filed Feb. 21, 2006.
U.S. Appl. No. 11/358,550, filed Feb. 21, 2006.
U.S. Appl. No. 11/358,681.
U.S. Appl. No. 11/358,818.
U.S. Appl. No. 11/358,861.
U.S. Appl. No. 11/505,055.
U.S. Appl. No. 11/505,166.
U.S. Appl. No. 11/505,178.

*Primary Examiner*—Elvis O Price
(74) *Attorney, Agent, or Firm*—Dominick G. Vicari

(57) ABSTRACT

A mercaptofunctional silane is provided of general Formula (1):

$$[HSG^1SiZ^\theta Z^\beta]_m[HSG^2SiZ^\beta{}_3]_n[HSG^3SiZ^\beta{}_2X]_o[[HSG^4SiZ^\beta X_2]_p \quad (1)$$

wherein the substituents are defined herein.

21 Claims, No Drawings

MERCAPTOFUNCTIONAL SILANE AND PROCESS FOR ITS PREPARATION

FIELD OF THE INVENTION

The present disclosure relates to mercaptofunctional silanes and their preparation. These silanes reduce or eliminate the generation of volatile organic compounds (VOC's) during use, aid in the processing of filled elastomeric materials and enhance the end-use properties of the filled elastomers.

DESCRIPTION OF THE RELATED ART

Mercaptosilanes and their use as coupling agents in filled elastomers are known in the art. However, the heretofore known silanes are very reactive with conventional fillers and elastomers and are therefore difficult to use. When known silanes are used at levels necessary to achieve optimum coupling of filler to the host elastomer, the uncured filled elastomer typically exhibits short scorch times and poorly dispersed filler. Long scorch times are necessary for mixing of the filler and other ingredients with the elastomer, extrusion of the uncured elastomer and fabrication of articles therefrom without premature crosslinking or formation of high viscosity compounds. Good dispersion of filler is required to achieve satisfactory end-use properties such as weatherability, wear, tear-resistance, and so on. Known silanes are also derived from monoalcohols that generate volatile organic compound (VOC) emissions during their fabrication and use.

U.S. Pat. Nos. 6,548,594 and 6,849,754 describe mercaptosilane coupling agents containing $C_9$-$C_{30}$ alkoxy groups. Although these compounds offer reduced VOC emissions, the processing of rubber containing them and their performance as coupling agents could stand improvement.

In addition to the need to reduce VOC's during the preparation of inorganic filled elastomers, there is also a need to improve the dispersion of the inorganic fillers in the elastomers while maintaining processability of the compositions. Better dispersion improves the performance of cured articles made with the filled elastomers, such as tires, by reducing their rolling resistance, heat build-up and wear.

Glycol derivatives of organosilanes are known in the art. Recently, the present inventors addressed in U.S. patent application Ser. Nos. 11/358,550, 11/358,818, 11/358,369, and 11/358,861 the scorch, VOC emissions and coupling performance of filled elastomers using organofunctional silanes or mixtures of organofunctional silanes that contain both blocked and free mercaptan groups. The present inventors also addressed in U.S. patent application Ser. Nos. 11/505,055, 11/505,166, and 11/505,178 the scorch, VOC emissions and coupling performance of filled elastomers using organofunctional silanes or mixtures of organofunctional silanes that contain both dispersing and free mercaptan groups. In addition, the present inventors addressed in U.S. patent application Ser. No. 11/104,103 the VOC emissions of organofunctional silanes containing alkanedioxysilyl groups. The entire contents of U.S. patent application Ser. Nos. 11/358,550; 11/358,818; 11/358,681; 11/505,055; 11/505,166; 11/505,178; and 11/104,103 are incorporated by reference herein.

However, there is still a need to further improve the coupling performance of organofunctioal silanes to impart better wear and reinforcing properties to elastomeric materials while maintaining low VOC emissions from the filled elastomeric materials and elastomeric articles during their preparation and use.

SUMMARY OF THE INVENTION

In one embodiment, the present invention provides mercaptofunctional silane of general Formula (1):

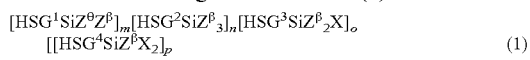

wherein:

each occurrence of $G^1$, $G^2$, $G^3$, and $G^4$ is independently a hydrocarbylene group containing from 1 to 30 carbon atoms selected from the group consisting of divalent groups derived by substitution of a hydrogen on alkyl, alkenyl, aryl, or aralkyl or a substituted divalent heterocarbon containing 2 to 30 carbon atoms and one or more etheric oxygen (—O—) and/or sulfur (—S—) atoms;

each occurrence of X is independently selected from the group consisting of —Cl, —Br, RO—, RC(=O)O—, $R_2$C=NO—, $R_2$NO—, —R, $(HO)_{d-1}G^5O$—, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^5$ is independently a hydrocarbylene group of from 2 to 15 carbon atoms or a divalent heterocarbon group of from about 4 to about 15 carbon atoms containing one or more etheric oxygen atoms;

each occurrence of $Z^\beta$, which forms a bridging structure between two silicon atoms, is $[—OG^5(OH)_{d-2}O—]_{0.5}$, wherein each occurrence of $G^5$ is independently selected form the group consisting of a hydrocarbylene group from 2 to 15 carbon atoms or a divalent heterocarbon group of from 4 to 15 carbon atoms containing one or more etheric oxygen atoms;

each occurrence of $Z^\theta$, which forms a cyclic structure with a silicon atom, is independently given by $—OG^5(OH)_{d-2}O—$, wherein $G^5$ is independently selected form the group consisting of a hydrocarbylene group of from 2 to 15 carbon atoms or a divalent heterocarbon group of from 4 to 15 carbon atoms containing one or more etheric oxygen atoms;

each occurrence of subscripts d, m, n, o and p independently is an integer wherein d is from 2 to 6 in a first embodiment, 2 or 3 in a second embodiment and 2 in a third embodiment; m is 0 to 20; n is 0 to 18; o is 0 to 20; and, p is 0 to 20, with the proviso that m+n+o+p is equal to or greater than 2.

DETAILED DESCRIPTION OF THE INVENTION

The expression "organofunctional silane" as used herein shall be understood to mean a dimeric, oligomeric or polymeric silane possessing mercaptan functionality and silane dimers, oligomers and/or polymers in which adjacent silane units are bonded to each other through bridged dialkoxysilane structures derived from polyhydroxy-containing compounds.

It will be understood that all ranges herein include all subranges therebetween. It will also be understood that all listings of members of a group can further comprise combinations of any two or more members of the group.

In accordance with the invention, mercaptofunctional silanes of general Formula (1) are prepared by the process which comprises reacting a) at least one mercaptofunctional silane selected from the group consisting of general Formulae (2), (3), (4) and (5):

wherein:

each occurrence of $G^1$, $G^2$, $G^3$, and $G^4$ is independently a hydrocarbylene group containing from 1 to 30 carbon atoms derived by substitution of a hydrogen on alkyl, alkenyl, aryl, or aralkyl or a divalent heterocarbon group containing 2 to 30 carbon atoms and one or more etheric oxygen (—O—) and/or sulfur (—S—) atoms;

each occurrence of X is independently selected from the group consisting of —Cl, —Br, RO—, RC(=O)O—, $R_2C$=NO—, $R_2NO$—, —R, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, with the proviso that at least one, and advantageously, two of X are hydrolyzable groups; with b) one or more polyhydroxy-containing compounds of general Formula (6):

$$G^5(OH)_d \qquad (6)$$

wherein $G^5$ is a hydrocarbyl group of from 2 to 15 carbon atoms or a heterocarbyl group of from 4 to 15 carbon atoms containing one or more etheric oxygen atoms and d is an integer of from 2 to 6, under tranesterification reaction conditions, thereby producing mercaptofunctional silane (1).

In one particular embodiment of the invention, the silane reactants are trialkoxysilanes represented by at least one of general Formulae (7) and (10):

$$(HS)\text{-}G^1\text{-}(SiOR)_3 \qquad (7)$$

$$(HS)\text{-}G^2\text{-}(SiOR)_3 \qquad (8)$$

$$(HS)\text{-}G^3\text{-}(SiOR)_3 \qquad (9)$$

$$(HS)\text{-}G^4\text{-}(SiOR)_3 \qquad (10)$$

wherein:

each occurrence of $G^1$, $G^2$, $G^3$, and $G^4$ is independently a hydrocarbylene group containing from 1 to 12 carbon atoms derived by substitution of a hydrogen on alkyl, alkenyl, aryl, or aralkyl;

each R independently has one of the aforestated meanings and, advantageously, is a methyl, ethyl, propyl, isopropyl, n-butyl or sec-butyl group.

In one embodiment herein, in a silane dimer, oligomer, or polymer, each silane unit of the dimer, oligomer or polymer is bonded to an adjacent silane unit through a bridging group resulting from the reaction of the selected silane monomer(s) with one or more polyhydroxy-containing compounds of general Formula (11):

$$G^5(OH)_d \qquad (11)$$

wherein $G^5$ is a hydrocarbyl group of from 2 to 15 carbon atoms or a heterocarbyl group of from 4 to 15 carbon atoms containing one or more etheric oxygen atoms and d is an integer of from 2 to 6, more specifically from 2 to 4, and still more specifically 2.

In one embodiment herein, polyhydroxy-containing compound of Formula (11) is a diol (glycol) of at least one of the general Formulae (12) and (13):

$$HO(R^0CR^0)_fOH \qquad (12)$$

$$HO(CR^0{}_2CR^0{}_2O)_eH \qquad (13)$$

wherein $R^0$ is independently given by one of the members listed above for R, f is 2 to 15 and e is 2 to 7.

Some representative non-limiting examples of such diols are $HOCH_2CH_2OH$, $HOCH_2CH_2CH_2OH$, $HOCH_2CH_2CH_2CH_2OH$, $HOCH_2CH(CH_3)CH_2OH$, $(CH_3)_2C(OH)CH_2CH(OH)CH_3$, $CH_3CH(OH)CH_2CH_2OH$, diols possessing an etheric oxygen-containing group such as $HOCH_2CH_2OCH_2CH_2OH$, $HOCH_2CH_2CH_2OCH_2CH_2CH_2OH$, $HOCH_2CH(CH_3)OCH_2CH(CH_3)OH$ and diols possessing a polyether backbone such $HOCH_2CH_2OCH_2CH_2OCH_2CH_2OH$, a diol of Formula (12) wherein $R^0$ is hydrogen or methyl and e is 3 to 7.

In another embodiment herein, polyhydroxy-containing compound of Formula (11) possesses higher hydroxyl functionality, such as triols and tetrols, of general Formula (14):

$$G^5(OH)_d \qquad (14)$$

wherein $G^5$ is a is a substituted hydrocarbyl group of from 2 to 15 carbon atoms or a substituted heterocarbon of from 4 to 15 carbon atoms containing one or more etheric oxygen atoms; and, d is an integer of from 3 to 6.

Some non-limiting examples of higher hydroxyl functionality compounds (14) include glycerol, trimethylolethane, trimethylolpropane, 1,2,4-butanetriol, 1,2,6-hexanetriol, pentaerythritol, dipentaerythritol, tripentaerythritol, mannitol, galacticol, sorbitol, and combinations thereof. Mixtures of polyhydroxy-containing compounds of Formulae (11)-(14) can also be used herein.

In one embodiment of the general preparative process described above, at least one mercaptofunctional trialkoxysilane selected from amongst Formulae (7), (8), (9) and/or (10) is transesterified with at least one diol of Formula (11), optionally, in the presence of a transesterification catalyst such as para-toluenesulfonic acid, to provide mercaptofunctional silane of Formula (1).

In one application of the foregoing embodiment of the general preparative process, at least one mercaptotrialkoxysilane of Formulae (7), (8), (9) and (10) wherein:

each occurrence of $G^1$, $G^2$, $G^3$, and $G^4$ is independently a hydrocarbylene group containing from 1 to 30 carbon atoms derived by substitution of a hydrogen on alkyl, alkenyl, aryl or aralkyl, more specifically a straight or branched chain alkylene group of from 1 to 6 carbon atoms, even more specifically from 1 to 3 carbon atoms, and still more specifically 3 carbon atoms;

each R is independently selected from the group consisting of straight, cyclic and branched alkyl, alkenyl, aryl and aralkyl containing up to 18 carbon atoms; is transesterified with at least one diol of Formula (12), wherein:

each occurrence of $R^0$ and f is independently given by one of the members listed above for R and hydrogen, and f is 2 to 15, more specifically, each occurrence of $R^0$ is independently selected from the group consisting of hydrogen and a straight or branched chain alkyl group of from 1 to 6 carbon atoms and f is an integer from about 2 to about 6, and even more specifically, each occurrence of $R^0$ is independently selected from the group consisting of a hydrogen and a straight or branched chain alkyl group from 1 to 3 carbon atoms and f is an integer of from 2 to 4, and more specifically, each occurrence of $R^0$ is independently selected from the group consisting of hydrogen and a straight chain alkyl group of 1 or 2 carbon atoms and with the proviso that at least one $R^0$ is an alkyl group and f is an integer of 2 or 3, optionally in the presence of transesterification catalyst such as the non-limiting example of para-toluenesulfonic acid, to provide a mercaptofunctional silane of Formula (1):

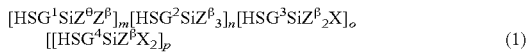
(1)

wherein:
each occurrence of $G^1$, $G^2$, $G^3$ and $G^4$ is independently a hydrocarbylene group containing from 1 to 30 carbon atoms derived by substitution of a hydrogen on alkyl, alkenyl, aryl, or aralkyl, more specifically a straight or branched chain alkylene group of from 1 to 6 carbon atoms, even more specifically from 1 to 3 carbon atoms and still more specifically 3 carbon atoms;

each occurrence of $Z^\beta$, which forms a bridging structure between two silicon atoms, is independently [—O($R^0CR^0$)$_f$O—]$_{0.5}$, wherein each occurrence of $R^0$ is independently given by one of the members listed above for R, and f is from 2 to 15, and more specifically each occurrence of $R^0$ is independently selected from the group consisting of hydrogen and a straight or branched chain alkyl group of from 1 to 6 carbon atoms and f is an integer from 2 to 6, and even more specifically, each occurrence of $R^0$ is independently selected from the group consisting of hydrogen and a straight or branched chain alkyl group of from about 1 to 3 carbon atoms and f is an integer of from 2 to 4, and most specifically, each occurrence of $R^0$ is independently selected from the group consisting of hydrogen and a straight chain alkyl group 1 or 2 carbon atoms and with the proviso that at least one $R^0$ is an alkyl group and f is an integer of 2 or 3;

each occurrence of $Z^\theta$, which forms a cyclic structure with a silicon atom, is independently —O($R^0CR^0$)$_f$O—, wherein each occurrence of $R^0$ is independently given by one of the members listed above for R, and f is 2 to 15, and more specifically each occurrence of $R^0$ is independently selected from the group consisting of hydrogen and a straight or branched chain alkyl group of from 1 to 6 carbon atoms and f is an integer of from 2 to 6, and even more specifically, each occurrence of $R^0$ is independently selected from the group consisting of hydrogen and a straight or branched chain alkyl group from 1 to 3 carbon atoms and f is an integer of from 2 to 4, and most specifically, each occurrence of $R^0$ is independently selected from the group consisting of hydrogen and a straight chain alkyl group of 1 or 2 carbon atoms and with the proviso that at least one $R^0$ is an alkyl group and f is an integer of 2 or 3;

each occurrence of X is independently —OR, wherein each occurrence of R is independently selected from the group consisting of straight, cyclic and branched alkyl, alkenyl, aryl and aralkyl containing up to 18 carbon atoms; and, each occurrence of m, n, o, and p independently is an integer wherein m is from 0 to 20, more specifically from 0 to 5 and even more specifically from 0 to 2; n is specifically from 0 to 18, more specifically from 0 to 4, and even more specifically from 0 to 2 and still more specifically 1 or 2; o is specifically from 0 to 20, more specifically from 0 to 5, even more specifically from 0 to 2 and still more specifically 1 or 2; p is specifically from 0 to about 20, more specifically from 0 to 5 and even more specifically from 0 to 2; with the proviso that m+n+o+p is equal to or greater than 2.

In another specific embodiment, each occurrence of m, n, o and p independently is an integer wherein m is from 0 to 2, n is from 0 to 2, o is from 0 to 2 and p is 0 to 2, more specifically, m is from 2 to 4, n is from 0 to 2, o is from 0 to 2 and p is 0 and even more specifically, m is 0, n is from 0 to 2, o is from 0 to 2 and p is 2 to 4, and still more specifically, m is 2, n is 0, o is 0 and p is 0, and still more specifically, m is 0, n is 0, o is 0 and p is 2.

In another specific embodiment, each occurrence of $G^1$, $G^2$, $G^3$ and $G^4$ independently is a divalent straight or branched chain alkylene group of from 1 to 6 carbon atoms, more specifically from 1 to 4 carbon atoms and still more specifically of 2 or 3 carbon atoms.

In another embodiment, $G^1$, $G^2$, $G^3$ and $G^4$ are the same hydrocarbylene group containing from 1 to 30 carbon atoms, more specifically the same straight or branched chain alkylene group of from about 1 to 6 carbon atoms, more specifically the same straight or branched chain alkylene group of from 1 to 4 carbon atoms and still more specifically the same straight chain alkylene group of 2 or 3 carbon atoms.

In another embodiment, at least one $G^1$, $G^2$, $G^3$ and $G^4$ group is different from the other $G^1$, $G^2$, $G^3$ and $G^4$ group and each occurrence of $G^1$, $G^2$, $G^3$ and $G^4$ independently is a hydrocarbylene group containing from 1 to 30 carbon atoms, more specifically a straight or branched chain alkylene group of from 1 to 6 carbon atoms, still more specifically a straight or branched chain alkylene group of from 1 to 4 carbon atoms and yet still more specifically a straight chain alkylene group of 2 or 3 carbon atoms.

Reaction conditions for preparing mercaptofunctional silanes of Formula (1) and their mixtures are fairly broad and include molar ratios of silane(s), determined by adding the individual molar contribution of silanes of Formulae (2), (3), (4) and/or (5), and polyhydroxy-containing compound(s) of Formula (6), of from about 0.3 to about 3 moles of compound of Formula (6) per mole of silyl group, more specifically from about 0.5 to about 2 moles of compound of Formula (6) per mole of silyl group, and still more specifically from about 1 to about 1.5 moles of Formula (6) per mole of silyl group, at a temperature of from about 0° C. to about 150° C., a pressure of from about 0.1 to about 2,000 mmHg, and in the optional presence of catalyst and/or solvent.

In another specific embodiment herein, there is provided mercaptofunctional and cyclic and/or bridging dialkoxy silane of Formula (1):

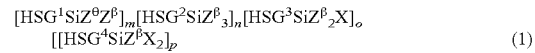
(1)

wherein:
each occurrence of $G^1$, $G^2$, $G^3$ and $G^4$ is independently a group derived by substitution of hydrogen on alkyl, alkenyl, aryl, or aralkyl having from 1 to about 30 carbon atoms;

each occurrence of X is independently selected from the group consisting of —Cl, —Br, RO—, RC(=O)O—, $R_2C$=NO—, $R_2NO$—, $R_2N$—, —R, $(HO)_{d-1}G^5O$—, $HO(CR^0_2)_fO$—, and $HO(CR^0_2CR^0_2O)_e$—, wherein each R is independently selected from the group consisting of hydrogen, straight, cyclic or branched alkyl that can, or does not, contain unsaturation, alkenyl groups, aryl groups, and aralkyl groups, wherein each R, other than hydrogen, contains from 1 to 18 carbon atoms, $G^5$ is independently a hydrocarbylene group of from 2 to 15 carbon atoms or a divalent heterocarbon group of from 4 to 15 carbon atoms containing one or more etheric oxygen atoms, $R^0$ is independently given by one of the members listed for R, f is 2 to 15 and e is 2 to 7;

each occurrence of $Z^\beta$, which forms a bridging structure between two silicon atoms, is independently selected from the group consisting of, [—OG$^5$(OH)$_{d-2}$O—]$_{0.5}$,

[—O(CR⁰₂CR⁰₂)ₑ—]₀.₅ and [—O(R⁰CR⁰)բO—]₀.₅, wherein each occurrence of R⁰ is independently given by one of the members listed above for R; and, each occurrence of G⁵ is independently selected form the group consisting of a substituted hydrocarbon group of from 2 to 15 carbon atoms or a substituted heterocarbon of from 4 to 15 carbon atoms and containing one or more etheric oxygen atoms;

each occurrence of Z⁰, which forms a cyclic structure with a silicon atom, is independently given by —OG⁵(OH)_{d-2}O—, —O(CR⁰₂CR⁰₂O)ₑ— and —O(R⁰CR⁰)բO— wherein each occurrence of R⁰ is independently given by one of the members listed above for R;

each occurrence of the subscripts, d, e, f, m, n, o and p is independently an integer wherein d is from 2 to 6, more specifically from 2 to 4 and still more specifically 2; e is from 2 to 7, more specifically from 2 to 4 and still more specifically 2; f is from about 2 to 15, more specifically from 2 to 4 and still more specifically 3; m is from 0 to 20, more specifically from 0 to 5 and still more specifically from 1 or 2; n is from 0 to 18, more specifically from 0 to 4 and still more specifically from 1 or 2; o is from 0 to 20, and specifically from 0 to 5, and still more specifically 1 to 2, and p is from 0 to 20, more specifically 0 to 5, and still more specifically from 0 to 2, with the proviso that m+n+o+p is equal to or greater than 2 and with the additional proviso that each of the above mercaptofunctional silanes of Formula (1) contains at least one hydrolysable group, Z^β or Z^Θ.

It will be appreciated that the structure, [—OG⁵(OH)_{d-2}(O—)]₀.₅ can further react with a third or more silyl groups to form bridging trialkoxysilyl, tetraalkoxysilyl groups, and so on, and are represented by [—OG⁵(OH)_{d-3}(O—)₂]_{1/3}, [—OG⁵(OH)_{d-4}(O—)₃]_{1/4}, and so on.

In accordance with another embodiment herein, a process for the preparation of a mercaptofunctional silane containing cyclic and/or bridging dialkoxysilyl groups is provided which comprises blending at least one mercaptofunctional silane selected from the group consisting of Formulae (2), (3), (4) and (5):

(HS)-G¹-(SiX₃)  (2)

(HS)-G²-(SiX₃)  (3)

(HS)-G³-(SiX₃)  (4)

(HS)-G⁴-(SiX₃)  (5)

wherein each occurrence of G¹, G², G³, G⁴ and X has one of the aforestated meanings and with the proviso that at least one of X is a hydrolyzable group; and transesterifying the mixture with one or more polyhydroxy-containing compounds of general Formula (6):

G⁵(OH)_d  (6)

wherein each occurrence of G⁵ and d have one of the aforestated meanings, advantageously in the presence of a transesterification catalyst.

In another embodiment, a process for the preparation of mercaptofunctional silane containing cyclic and/or bridging dialkoxy silyl groups is provided which comprises blending at least one mercaptofunctional silane selected from the group consisting of the Formulae (2), (3), (4) and (5):

(HS)-G¹-(SiX₃)  (2)

(HS)-G²-(SiX₃)  (3)

(HS)-G³-(SiX₃)  (4)

(HS)-G⁴-(SiX₃)  (5)

wherein each occurrence of G¹, G², G³, G⁴ and X has one of the aforestated meanings and with the proviso that at least one of X is a hydrolyzable group; and transesterifying the mixture with one or more diols of general Formulae (12) and (13):

HO(R⁰CR⁰)բOH  (12)

HO(CR⁰₂CR⁰₂O)ₑH  (13)

wherein R⁰, e, and f have one of the aforestated meanings.

In one embodiment herein in connection with silanes of Formula (1), the terms "diol" and "difunctional alcohol" refer to any structure of general Formula (12):

HO(R⁰CR⁰)բOH  (12)

wherein f and R⁰ are as defined herein. These structures include hydrocarbons in which two hydrogen atoms are replaced with —OH in accordance with compounds of Formula (11), supra.

In another embodiment herein in connection with silanes of Formula (1), "dialkoxy" and "difunctional alkoxy" refer to hydrocarbon-based diols in which the two OH hydrogen atoms have been removed to give divalent radicals, and whose structures are represented by general Formula (14):

—O(R⁰CR⁰)բO—  (14)

wherein f and R⁰ are as defined herein.

In yet another embodiment herein in connection with silanes of Formula (1), "cyclic dialkoxy" refers to a silane or group in which cyclization is about a silicon atom by two oxygen atoms each of which is attached to a common divalent hydrocarbon group such as is commonly the case with diols. In one embodiment cyclic, dialkoxy groups herein are represented by Z^Θ which is important in the formation of the cyclic structure. In yet another embodiment, R⁰ groups that are more sterically hindered than hydrogen promote the formation of cyclic structures. In yet a further more embodiment the formation of cyclic structures is also promoted when the value of f in the diol of Formula (12) is 2 or 3, and more specifically 3.

In yet a further embodiment herein in connection with silanes of Formula (1), "bridging dialkoxy" refers to a silane or group in which two different silicon atoms are each bound to one oxygen atom, which in turn is bound to a common divalent hydrocarbon group such as is commonly found in diols. Bridging dialkoxy groups herein are represented by Z^β.

In yet still a further embodiment herein in connection with silanes of Formula (1), "hydroxyalkoxy" refers to a silane or group in which one OH hydrogen atom has been removed to provide a monovalent radical, and whose structures are represented by general Formulae (15), (16) and (17):

(HO)_{d-1}G⁵O—  (15)

HO(R⁰CR⁰)բO—  (16)

HO(CR⁰₂CR⁰₂O)ₑ—  (17)

wherein G⁵, e, f and R⁰ are defined above. Hydroxyalkoxy groups herein are represented by X.

In yet another embodiment herein in connection with silanes of Formula (1), the term "hydrocarbon based diols" refers to diols that contain two OH groups as part of a hydrocarbon structure. In another embodiment, absent from these hydrocarbon based diols are heteroatoms (other than the oxygens in the OH groups), in particular ether groups. In one embodiment, hydrocarbon diols that contain heteroatoms, such as oxygen, are represented by Formula (13):

$$HO(CR^O_2CR^O_2O)_e—H \qquad (13).$$

In another embodiment, these diols are not as likely to form cyclic structures with the silyl group because of the size of the ring being 8 atoms or larger, which are less likely to form than rings that contain 5 or 6 atoms.

Structures of Formula (12) will be referred to herein as either "the appropriate diol" or "glycol" prefixed by the particular hydrocarbon group associated with the two OH groups. In one specific embodiment, some non-limiting examples of Formula (12) include neopentylglycol, 1,3-butanediol, 2-methyl-1,3-propanediol and 2-methyl-2,4-pentanediol.

Structures of Formula (14) will be referred to herein as the appropriate dialkoxy, prefixed by the particular hydrocarbon group associated with the two OH groups, for example, the diols neopentylglycol, 1,3-butanediol and 2-methyl-2,4-pentanediol correspond herein to the dialkoxy groups neopentylglycoxy, 1,3-butanedialkoxy, 2-methyl-1,3-propanedialkoxy and 2-methyl-2,4-pentanedialkoxy, respectively.

In connection with $Z^\beta$, the notations $[—OG^5(OH)_{d-2}O—]_{0.5}$, $[—O(R^OCR^O)_fO—]_{0.5}$, and $[—O(CR^O_2CR^O_2O)_e—]_{0.5}$ refer to one-half of a bridging dialkoxy group which can connect to different silyl groups present in the mercaptofunctional silanes of Formula (1). These notations are used in conjunction with a silicon atom and they are taken herein to mean that one-half of a dialkoxy group is bound to the associated silicon atom. It is understood that the other half of the dialkoxy group is bound to a silicon atom that occurs somewhere else in the overall molecular structure being described. Thus, in one embodiment, the $[—OG^5(OH)_{d-2}O—]_{0.5}$, $[—O(R^OCR^O)_fO—]_{0.5}$ and $[—O(CR^O_2CR^O_2O)_e—]_{0.5}$ dialkoxy groups mediate the chemical bonds that hold two separate silicon atoms together, whether these two silicon atoms occur intermolecularly or intramolecularly. In one embodiment, in the case of $[—O(R^OCR^O)_fO—]_{0.5}$ and $[—O(CR^O_2CR^O_2O)_e—]_{0.5}$, if the group $(R^OCR^O)_f$ and $(CR^O_2CR^O_2O)_e$ are unsymmetrical, either end of $[—O(R^OCR^O)_fO—]_{0.5}$ and $[—O(CR^O_2CR^O_2O)_e—]_{0.5}$ can be bound to either of the two silicon atoms required to complete the structures of silanes of Formula (1).

In still a further embodiment herein in connection with silanes of Formulae (1), (2), (3), (4), (5), (7), (8), (9), and (10), "alkyl" includes straight, branched and cyclic alkyl groups; "alkenyl" includes any straight, branched, or cyclic alkenyl group containing one or more carbon-carbon double bond, where the point of substitution can be either at a carbon-carbon double bond or elsewhere in the group; "aryl" includes the non-limiting group of any aromatic hydrocarbon from which one hydrogen atom has been removed; "aralkyl" includes, but is not limited to, any of the aforementioned alkyl groups in which one or more hydrogen atoms have been substituted by the same number of like and/or different aryl (as defined herein) substituents. Specific examples of alkyls include, but are not limited to, methyl, ethyl, propyl and isobutyl. Specific examples of alkenyls include, but are not limited to, vinyl, propenyl, allyl, methallyl, ethylidenyl norbornane, ethylidene norbornyl, ethylidenyl norbornene and ethylidene norbornenyl. Specific examples of aryls include, but are not limited to, tolyl, xylyl, phenyl and naphthalenyl. Specific examples of aralkyls include, but are not limited to, benzyl and phenethyl.

In another embodiment herein, in connection with silanes of Formula (1), (2), (3), (4), (5), (7), (8), (9), and (10), "cyclic alkyl", "cyclic alkenyl", also include bicyclic, tricyclic, and higher cyclic structures, as well as the aforementioned cyclic structures further substituted with alkyl, alkenyl, groups. Representative examples of "cyclic alkyl", "cyclic alkenyl", include, but are not limited to, norbornyl, norbornenyl, ethylnorbornyl, ethylnorbornenyl, ethylcyclohexyl, ethylcyclohexenyl, cyclohexylcyclohexyl and cyclododecatrienyl.

In another embodiment herein, the silane is one described by Formula (1) in which $G^1$, $G^2$, $G^3$ and $G^4$ is independently a divalent group derived by substitution of $C_1$-$C_{12}$ alkyl; X is —R and/or —OR, wherein R is methyl, ethyl and/or —O(R^OCR^O)_fOH; $Z^\beta$ is $[—O(R^OCR^O)_fO—]_{0.5}$ and $Z^\theta$ is —O(R^OCR^O)_fO— wherein $R^O$ is hydrogen or methyl, f is 2 or 3 and m, n, o and p are 0 to 2, with the proviso that m+n+o+p is equal to or greater than 2.

In still another embodiment herein, the silane is one described by Formula (1) in which $G^1$, $G^2$, $G^3$ and $G^4$ is independently a divalent group derived by substitution of $C_3$-$C_6$ straight chain alkyl; X is —OR, wherein R is ethyl or —O(R^OCR^O)_fOH; $Z^\beta$ is $[—O(R^OCR^O)_fO—]_{0.5}$ and $Z^\theta$ is —O(R^OCR^O)_fO— wherein $R^O$ is hydrogen or methyl, f is 2 or 3 and m, n, o and p are 0 to 2, with the proviso that m+n+o+p is equal to or greater than 2.

Some representative examples of $G^1$, $G^2$, $G^3$ and $G^4$ include, but are not limited to those selected from the group consisting of branched alkylene groups of 1 to 30 carbon atoms and include the non-limiting examples such as —$CH_2$(CH_2)_4CH(CH_2CH_3)CH_2—, —$CH_2CH_2CH(CH_2CH_3)CH_2$—, —$CH_2CH(CH_3)CH_2$—, —$CH_2CH_2CH(CH_3)CH_2$—, and —$CH_2(CH_2)_4CH(CH_3)CH_2$—; diethylene cyclohexane; phenylene; any of the structures derivable from divinylbenzene, such as the non-limiting examples of —$CH_2CH_2(C_6H_4)CH_2CH_2$— and —$CH_2CH_2(C_6H_4)CH(CH_3)$—, where the notation $C_6H_4$ denotes a disubstituted benzene ring; any of the structures derivable from dipropenylbenzene, such as the non-limiting examples of —$CH_2CH(CH_3)(C_6H_4)CH(CH_3)CH_2$—, where the notation $C_6H_4$ denotes a disubstituted benzene ring; any of the structures derivable from piperylene, such as the non-limiting examples of —$CH_2CH_2CH_2CH(CH_3)$—, —$CH_2CH_2CH(CH_2CH_3)$—, and —$CH_2CH(CH_2CH_2CH_3)$—; any of the isomers of —$CH_2CH_2$-norbornyl-; any of the monounsaturated structures derivable from myrcene containing a trisubstituted C=C, such as the non-limiting examples of —$CH_2CH_2CH_2CH=C(CH_3)_2]CH_2CH_2$—, —$CH_2CH[CH_2CH_2CH=C(CH_3)_2]CH(CH_3)$—, —$CH_2C[CH_2CH_2CH=C(CH_3)_2](CH_2CH_3)$—, —$CH_2CH_2CH[CH_2CH_2CH=C(CH_3)_2]CH_2$—, —$CH_2CH_2(C—)(CH_3)[CH_2CH_2CH=C(CH_3)_2]$, and —$CH_2CH[CH(CH_3)[CH_2CH_2CH=C(CH_3)_2]]$—; and any of the monounsaturated structures derivable from myrcene lacking a trisubstituted C=C, such as the non-limiting examples of —$CH_2CH(CH=CH_2)CH_2CH_2CH_2C(CH_3)_2$—, —$CH_2CH(CH=CH_2)CH_2CH_2CH[CH(CH_3)_2]$—, —$CH_2C(=CH—CH_3)CH_2CH_2CH_2C(CH_3)_2$—, —$CH_2C(=CH—CH_3)CH_2CH_2CH[CH(CH_3)_2]$—, —$CH_2CH_2C(=CH_2)CH_2CH_2CH_2C(CH_3)_2$—, —$CH_2CH_2C(=CH_2)CH_2CH_2CH[CH(CH_3)_2]$—, —$CH_2CH=C(CH_3)CH_2CH_2CH_2C(CH_3)_2$— and —$CH_2CH=C(CH_3)_2CH_2CH_2CH[CH(CH_3)_2]$; —$(CH_2)_g$— wherein g is an integer of from 1 to 30, which represent terminal straight-chain alkyls further substituted terminally at the other end, such as the non-limiting examples of —$CH_2$—, —$CH_2CH_2$—, —$CH_2CH_2CH_2$—, and —$CH_2CH_2CH_2CH_2CH_2CH_2$—; their beta-substituted analogs, such as —$CH_2(CH_2)_iCH(CH_3)$—, where i is preferably 0 to 16; methyl substituted alkylene groups such as the non-limiting examples of —$CH_2CH_2$-methylcyclohexyl-, —CH₂CH₂C(CH₃)₂CH₂—, —CH₂CH(CH₃)CH₂—; any of the structures derivable from isoprene, such as —CH₂CH(CH₃)CH₂CH₂—, —CH₂CH(CH₃)CH(CH₃)—, —CH₂C(CH₃)(CH₂CH₃)—, —CH₂CH(CH₃)CH₂—, —CH₂CH₂C(CH₃)₂— and —CH₂CH[CH(CH₃)₂]—; any structure derivable from methallyl chloride; any of the structures derivable from butadiene, such as the non-limiting examples of —CH₂CH₂CH₂CH₂—, —CH₂CH₂CH(CH₃)—, and —CH₂CH(CH₂CH₃)—; and, any of the diradicals obtainable from norbornane, cyclohexane, or cyclopentane, by loss of two hydrogen atoms.

In yet another embodiment herein, $G^1$, $G^2$, $G^3$ and $G^4$ is —CH₂CH₂CH₂—, X is —OCH₂CH(CH₃)CH₂OH and $Z^\beta$ is [—OCH₂CH(CH₃)CH₂O—]$_{0.5}$ and and $Z^\theta$ is —OCH₂CH(CH₃)CH₂O—.

In yet a further embodiment, some representative non-limiting examples of R and $R^0$ groups are hydrogen, branched and straight-chain alkyls of 1 to 18 carbon atoms or more, such as the non-limiting examples of methyl, ethyl, propyl, isopropyl, butyl, octenyl, cyclohexyl, phenyl, benzyl, tolyl and allyl.

In one embodiment, R groups are selected from $C_1$ to $C_4$ alkyls and hydrogen and $R^0$ groups are selected from hydrogen, methyl, ethyl and propyl.

In one other embodiment, some specific non-limiting examples of X are methoxy, ethoxy, isobutoxy, propoxy, isopropoxy, acetoxy, oximato, monovalent hydroxyalkoxy groups derived from diols, —O(R⁰CR⁰)$_f$OH where $R^0$ and f is defined as herein, such as the non-limiting examples of 2-hydroxyethoxy, 2-hydroxypropoxy, 3-hydroxy-2,2-dimethylpropoxy, 3-hydroxypropoxy, 3-hydroxy-2-methylpropoxy, 3-hydroxybutoxy, 4-hydroxy-2-methylpent-2-oxy, and 4-hydoxybut-1-oxy and monovalent ether alkoxy groups of general Formulae (18), (19), and (20):

  (18)

  (19)

  (20)

wherein $R^1$ is independently selected from the group consisting of straight, cyclic or branched alkyl groups, alkenyl groups, aryl groups and aralkyl groups that contain from 1 to 18 carbon atoms; and $R^0$, $G^5$, e and f are defined as herein. In one embodiment X can also be a monovalent alkyl group, such as the non-limiting examples of methyl and ethyl.

In a specific embodiment, X is one of the non-limiting examples of methoxy, ethoxy, acetoxy, methyl, ethyl, 2-hydroxyethoxy, 2-hydroxypropoxy, 3-hydroxy-2,2-dimethylpropoxy, 3-hydroxypropoxy, 3-hydroxy-2-methylpropoxy, 3-hydroxybutoxy, 4-hydroxy-2-methylpent-2-oxy, and 4-hydoxybut-1-oxy.

In one embodiment, some specific non-limiting examples of $Z^\beta$ and $Z^\theta$ are the divalent alkoxy groups derived from diols such as ethylene glycol, propylene glycol, neopentyl glycol, 1,3-propanediol, 2-methyl-1,3-propanediol, 1,3-butanediol, 2-methyl-2,4-pentanediol, 1,4-butanediol, cyclohexane dimethanol and pinacol. In another embodiment, some more specific non-limiting examples of $Z^\beta$ and $Z^\theta$ are divalent alkoxy groups derived from ethylene glycol, propylene glycol, neopentyl glycol, 1,3-propanediol, 2-methyl-1,3-propanediol, 1,3-butanediol and 2-methyl-2,4-pentanediol.

In one specific embodiment herein, $Z^\beta$ and $Z^\theta$ are divalent alkoxy groups derived from 1,3-propanediol, 2-methyl-1,3-propanediol, 1,3-butanediol, and 2-methyl-2,4-pentanediol and combinations thereof. In one embodiment, the cyclic dialkoxy content of the silanes herein should be kept sufficiently high relative to the total dialkoxy content present to prevent excessive crosslinking, which would lead to gellation. In one embodiment herein, the cyclic dialkoxy silyl content of the silanes can be from about 10 to about 100 mole percent of the total concentration of silyl groups, specifically from about 25 to about 90 mole percent of the total concentration of silyl groups and more specifically from about 50 to about 70 mole percent of the total concentration of silyl groups. In another embodiment herein, excessive crosslinking can also be avoided if X in the structure of Formula (1) is large, such as for example, is the case when o and p are from about 1 to about 5 and/or when the number of fragments, [HSG²Z$^\beta$₃], in the structure of Formula (1) is low, specifically, when o is 0 and 1.

In yet a further embodiment, some representative non-limiting examples of the mercaptofunctional silanes herein, such as those that contain cyclic and/or bridging dialkoxysilyl groups and mercapto groups include, but are not limited to, 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propane-1-thiol; 3-(2-{3-[2-(3-mercapto-propy)-4,4,6-trimethyl-[1,3,2]dioxasilinan-2-yloxy]-2-methyl-propoxy}-4,4,6-trimethyl-[1,3,2]dioxasilinan-2-yl)-propane-thiol; 3-(2-{3-[2-(3-mercapto-propyl)-4,4,6-trimethyl-[1,3,2]dioxasilinan-2-yloxy]-1,1-dimethyl-butoxy}-4,4,6-trimethyl-[1,3,2]dioxasilinan-2-yl) -propane-1-thiol; 3-({3-[2-mercapto-propyl)-5-methyl-[1,3,2] dioxasilinan-yloxy]-2-methyl-propoxy}-bis-[3-hydroxy-2-methyl-propoxy]-silanyl)-propane-1-thiol; 3-[{3-[{3-bis-(3-hydroxy-2-methyl-propyl)-(3-mercapto-propyl)-silanyloxy]-1-methyl-propoxy}-(3-hydroxy-2-methyl-propoxy)-(3-mercapto-propyl)-silanyloxy]-2-methyl-propan-1-ol; 3-[[3-((3-hydroxy-3-methyl-propoxy)-3-mercapto-propyl)-{3-[2-(3-mercapto-propyl)-5-methyl-[1,3,2]dioxasilinan-2-yloxy]-1-methyl-propoxy}-silanyloxy)-2-methyl-propoxy-(3-hydroxy-2-methyl-propoxy)-3-mercapto-propyl)-silanyl(−2-methylpropan-1-ol; 3-(2-{3-[2-(3-mercapato-butyl)-[1,3,2]dioxasilinan-2-yloxy]-propoxy}-[1,3,2]dioxasilinan-2-yl)-butane-1-thiol; 3-(2-{3-[2-(3-mercapto-phenyl)-4,4,6-trimethyl-[1,3,2]dioxasilinan-2-yloxy]-2-methyl-propoxy}-4,4,6-trimethyl-[1,3,2]dioxasilinan-2-yl)-3-benzene-thiol; 3-(2-{3-[2-(3-mercapto-cyclohexyl)-4,4,6-trimethyl-[1,3,2]dioxasilinan-2-yloxy]-1,1-dimethyl-butoxy}-4,4,6-trimethyl-[1,3,2]dioxasilinan-2-yl)-cyclohexane-1-thiol; 3-({3-[2-mercapto-methyl)-5-methyl-[1,3,2]dioxasilinan-2-yloxy]-2-methyl-propoxy}-diethoxy]-silanyl)-methane-1-thiol; 3-[{3-[3-bis-(3-hydroxy-2,2-dimethyl-propyl)-(3-mercapto-propyl)-silanyloxy]-2,2-dimethyl-propoxy}-(3-hydroxy-2,2-dimethyl-propoxy)-(3-mercapto-propyl)-silanyloxy]-2,2-dimethyl-propan-1-ol; 3-[[3-((3-hydroxy-3-phenyl-propoxy)-3-mercapto-propyl)-{3-[2-(3-mercapto-propyl)-5-phenyl-[1,3,2]dioxasilinan-2-yloxy]-2-phenyl-1-propoxy}-silanyloxy)-2-phenyl-propoxy-(3-hydroxy-2-phenyl-propoxy)-3-mercapto-propyl)-silanyl]-2-phenylpropan-1-ol; 3-[{3-[(methyl)-(3-hydroxy-2-methyl-propoxy)-(3-mercapto-propyl)-silanyloxy]-2-methyl-propoxy}-methyl)-(3-mercapto-propyl)-silanyloxy]-2-methyl-propan-1-ol, and combinations thereof.

Moreover, in one other embodiment herein, it is understood that these silane compositions can also contain mercaptofunctional and monofunctional alkoxy groups. In a further embodiment herein, mercaptofunctional silanes containing only monofunctional alkoxy groups can be used as reagents in the preparation of the silanes herein. However, it is understood in one embodiment that these monofunctional alkoxy groups can contribute to VOC emissions during use if the monofunctional alcohols that are form upon hydrolysis of the silanes have high vapor pressure at room temperature. In a further embodiment, some non-limiting examples of high boiling monofunctional alkoxy groups, are those such as the alkoxy groups whose structures are represented by general Formula (20)

$$R^1O(CR^0{}_2CR^0{}_2O)_e— \tag{20}$$

wherein $R^0$, $R^1$ and e are defined as herein. In another embodiment, moreover, it is understood that the partial hydrolyzates and/or condensates of these cyclic and/or bridging mercaptofunctional silanes (i.e., cyclic and/or bridging dialkoxy mercaptofunctional and siloxanes and/or silanols) can also be encompassed by the silanes herein, in that these partial hydrolyzates and/or condensates will be a side product of most methods of manufacture of the silanes described herein or can occur upon storage, especially in humid conditions, or under conditions in which residual water remaining from their preparation is not completely removed subsequent to their preparation.

Furthermore in another specific embodiment, partial to substantial hydrolysis of silanes of Formula (1) will form silanes that contain siloxane bonds, i.e., $Z^\beta=(—O—)_{0.5}$, and are encompassed by the silanes described herein; and in a more specific embodiment they can be deliberately prepared by incorporating the appropriate stoichiometry or an excess of water into the methods of preparation described herein for the silanes. In one embodiment, silane structures herein encompassing hydrolyzates and siloxanes are described in the structures represented by Formula (1) wherein $Z^\beta=(—O—)_{0.5}$ and/or $X^\alpha=OH$ are substantive (i.e., substantially larger than zero), for example, the ratio of $(—O—)_{0.5}$ to $[—OG^5(OH)_{d-2}O—]_{0.5}$ is specifically from 1 to 99, more specifically from 1 to 20, and still more specifically from 1 to 5, and with the proviso that the silane of Formula (1) contains at least one $Z^\beta$ that is $[—OG^5(OH)_{d-2}O—]_{0.5}$ or at least one $Z^\theta$ that is $—OG^5(OH)_{d-2}O—$. In one embodiment herein, the ratio of siloxane bridging group, $(—O—)_{0.5}$, to dioxy bridging group, $[—O(R^0CR^0)_fO—]_{0.5}$, is within a range of from about 0 to about 1. In another embodiment, the ratio is within a range of from about 0 to about 0.2. In a further embodiment, the ratio is within a range of from about 0.05 to about 0.15.

In another embodiment herein, the mercaptofunctional silanes herein, including their mixtures, can be loaded on a particulate carrier such as porous polymer, carbon black, a siliceous material such as silica, and the like, so that they are in solid form for addition to rubber in a rubber compounding operation.

In a further embodiment herein, mercaptofunctional silanes of Formula (1) herein and mixtures thereof can be prepared by the general preparative process described as herein of which there are numerous specific embodiments. Generally, in one embodiment, the process for making one or a mixture of silanes of Formula (1) involve a transesterification reaction between one or more alkoxysilanes of Formulae (2), (3), (4) and (5) and one or more polyhydroxy-containing compounds of Formulae (6), (11), (12) and (13).

In one embodiment, the process for preparing mercaptofunctional silane of Formula (1) comprises:
a) mixing at least one mercaptosilanes of general Formulae (2), (3), (4) and/or (5): wherein each occurrence of $G^1$, $G^2$, $G^3$, $G^4$, and X are defined as herein, and with the proviso that at least one of X is a hydrolyzable group; and
b) transesterifying this mixture with at least one diol having the structure $G^5(OH)_d$, $HO(R^0CR^0)_fOH$, or $HO(CR^0{}_2CR^0{}_2O)_e—H$, optionally in the presence of a transesterification catalyst; and removing the X—H group that is formed; wherein each occurrence of $G^5$, $R^0$, d, e and f are defined as herein.

In one embodiment, the first reaction can be carried out by reacting a mixture of mercaptofunctional alkoxy silane with a diol at a molar ratio of about 0.5 mole to about 3.0 moles of diol per 1 mole of silyl group to be transesterified. In another embodiment, the ratio can range from about 1.0 to about 2.5 for a trialkoxysilyl group. In yet a further embodiment, the ratio can range from about 1.5 to about 2.0 for a trialkoxysilyl group. In one embodiment, the reaction can be carried out at a temperature ranging from about 0 to about 150° C., more specifically from about 25° C. to about 100° C. and still more specifically from about 60° C. to about 80° C., and all subranges therebetween, while maintaining a pressure in the range of from about 0.1 to about 2000 mm Hg absolute. In one embodiment, the temperature can range from about 30° C. to about 90° C. and all subranges therebetween. In another embodiment, the pressure can range from about 1 to about 80 mm Hg absolute. As those skilled in the art will recognize, in one embodiment, excess diol can be utilized to increase reaction rate, but it is not necessary under these conditions as it can increase the cost. In another embodiment, the reaction can be carried out by slowly adding diol to the mixture of the mercaptofunctional alkoxysilane at the desired reaction temperature and vacuum. In another embodiment, as the lower boiling X—H group, such as monoalcohol, is formed, it can be removed from the reaction mixture by a distillation cycle and removal of the mono alcohol helps drive the reaction to completion. In one embodiment, the reactions optionally can be catalyzed using a transesterification catalyst. In yet a further embodiment, suitable tranesterification catalysts are strong protic acids whose pKa are below 5.0, transition metal complexes such as complexes of tin, iron, titanium and other metal catalysts. In one embodiment, catalysts suitable for these reaction are disclosed in, "The Siloxane Bond, Physical Properties and Chemical Transformations", M. G. Voronkov, V. P. Mileshkevich and Yu. A. Yuzhelevskii, Consultants Bureau, a division of Plenum Publishing Company, New York (1978), Chapter 5 and is incorporated by reference herein in its entirety. In a further embodiment, strong bases are generally unsuitable as transesterification catalysts since they promote the reaction of the mercaptofunctional group with the diol and result in the formation of sulfides. In one embodiment, the acid or metal catalysts can be used at a range of from about 10 ppm to about 2 weight percent, specifically from about 20 ppm to about 1000 ppm, and more specifically of from about 100 ppm to about 500 ppm.

In a further embodiment herein, the final mixture can optionally be buffered after the reaction is complete. In one specific embodiment, buffering the mixture will neutralize the strong protic acids and thereby be less corrosive to metals and add to long-term product stability. In a still further specific embodiment, buffering can be conducted through methods and compounds known in the art.

In one specific embodiment, the products of the transesterification of mercaptofunctional silane (2), (3), (4) and/or (5) can comprise a considerable fraction of monomeric material in addition to the formation of dimers and other cyclic and/or bridged oligomers as illustrated by low viscosity reaction products. In one specific embodiment the fraction of monomeric material is from about 1 to about 99 mole percent, more specifically from about 10 to about 50 mole percent, and still more specifically from about 15 to about 25 mole percent.

In a further embodiment, the process for making the mercaptofunctional silane compositions herein can optionally employ an inert solvent. In a specific embodiment, the solvent can serve as a diluent, carrier, stabilizer, refluxing aid or heating agent. In a more specific embodiment, generally, any inert solvent that does not enter into the reaction or adversely affect the preparative process can be used. In one embodiment, the solvents are liquid under normal conditions and have a boiling point below about 150° C. In a more specific embodiment, some non-limiting examples of suitable solvents include aromatic or aliphatic hydrocarbon, ether, aprotic, or chlorinated hydrocarbon solvents such as toluene, xylene, hexane, butane, diethyl ether, dimethylformamide, dimethyl sulfoxide, carbon tetrachloride, methylene chloride, and combinations thereof.

In one embodiment herein, the process of transesterifying the mercaptoalkoxysilane with polyhydroxy-containing compound can be conducted continuously. In one more embodiment, in the case of a continuous operation, the process comprises:

a) reacting, in a thin film reactor, a thin film reaction medium comprising a mixture of at least one silane of Formulae (2), (3), (4) and/or (5), with at least one polyhydroxy-containing compound of Formula (6) and, optionally, transesterification catalyst, to provide mercaptofunctional silanes that contains a cyclic and/or bridged dialkoxy group, and by-product monoalcohol;

b) vaporizing by-product monoalcohol from the thin film to drive the reaction;

c) optionally, recovering by-product monoalcohol by condensation;

d) recovering the organofunctional silane reaction product(s); and, e) optionally, neutralizing the reaction medium to improve the storage stability of the mercapto functional silane product(s) therein.

In one embodiment herein, the molar ratio of polyhydroxy-containing compound to the mixture of mercaptofunctional silanes used in the continuous thin film process will depend upon the number of alkoxy groups that are desired to be replaced with a polyhydroxy-containing group, such as the non-limiting example of a diol (glycol). In one more specific embodiment, theoretically, a molar ratio of about 1.5 mole of diol of Formula (11) or (12) is required per mole of alkoxysilyl group to be transesterified to replace all of the mono alkoxy or other hydrolysable X— groups. In another embodiment herein, a molar ratio of from about 0.5 to about 1.0 moles of diol can be used per mole of alkoxy-silyl group. In a further embodiment, and, in many cases, additional diol is desirable because in some cases only one of the hydroxyl groups of the diol reacts with the alkoxysilyl group. In one embodiment these diols that react only once with a silyl group are defined as X in Formulae (1). In a further embodiment, the diols, referred to herein as "hydroxyalkoxy", reduce the viscosity and inhibit the gelation of the silane. In a still further embodiment and as one skilled in the art will readily recognize that excess diol can be utilized to increase reaction rates.

In one specific embodiment, the method of forming the film can be any of those known in the art. In a more specific embodiment, typical known devices include but are not limited to, falling film or wiped film evaporators. In one specific embodiment, minimum film thickness and flow rates will depend on the minimum wetting rate for the film forming surface. In another specific embodiment, maximum film thickness and flow rates will depend on the flooding point for the film and device. In a still further specific embodiment, the alcohol is vaporized from the film by heating the film, by reducing pressure over the film, or by a combination of both. In one embodiment, mild heating and reduced pressure are utilized to form the structures described herein. In yet a further embodiment, optimal temperatures and pressures (partial vacuum) for running the processes described herein will depend upon the specific mercaptofunctional silane's alkoxy groups and the diol used in the process. In yet an even further embodiment, additionally if an optional inert solvent is used in the process, that choice will affect the optimal temperatures and pressures (partial vacuum) utilized. In one specific embodiment, some non-limiting examples of such solvents include those listed herein. In one embodiment herein, the by-product X—H, such as a monofunctional alcohol, vaporized from the film is removed from the reactive distillation device by a standard partial vacuum-forming device and can be condensed, collected, and recycled as feed to other processes. In one embodiment, the silane product is recovered by standard means from the reactive distillation device as a liquid phase. In another embodiment, if an inert solvent has been used or if additional purification is necessary, the silane product can be fed to another similar distillation device or distillation column to effect that separation. In still another specific embodiment, optionally the transesterified reaction products can be neutralized to improve product storage.

In one more specific embodiment, if a protic catalyst is used to promote the transesterification of the silanes with diol, it can be useful to neutralize the catalyst with a base to improve the product's stability; however, only a stoichiometric amount of base is required to neutralize the protic catalyst; larger amounts of base will promote undesirable side reactions.

Further, in another embodiment, a free-flowing filler composition is provided which comprises:

a) at least one particulate filler; and, b) a mercaptofunctional silane composition comprising at the silane of Formula (1):

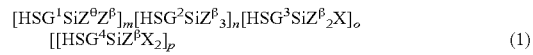

$$[HSG^1SiZ^\theta Z^\beta]_m[HSG^2SiZ^\beta{}_3]_n[HSG^3SiZ^\beta{}_2X]_o [[HSG^4SiZ^\beta X_2]_p \quad (1)$$

wherein:

each occurrence of $G^1$, $G^2$, $G^3$, and $G^4$ are independently a hydrocarbylene group containing from 1 to 30 carbon atoms derived by substitution of a hydrogen on alkyl, alkenyl, aryl, or aralkyl or a divalent heterocarbon containing 2 to 30 carbon atoms and one or more etheric oxygen (—O—) and/or sulfur (—S—) atoms;

each occurrence of X is independently selected from the group consisting of —Cl, —Br, RO—, RC(=O)O—, $R_2C$=NO—, $R_2NO$—, —R, $(HO)_{d-1}G^5O$—, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^5$ is independently a substituted hydrocarbylene group of from 2 to 15 carbon atoms or a substituted heterocarbon group of from 4 to 15 carbon atoms and containing one or more etheric oxygen atoms;

each occurrence of $Z^\beta$, which forms a bridging structure between two silicon atoms, is $[—OG^5(OH)_{d-2}O—]_{0.5}$, wherein each occurrence of $G^5$ is independently selected form the group consisting of a substituted hydrocarbylene group of from 2 to 15 carbon atoms or a substituted heterocarbon of from 4 to 15 carbon atoms and containing one or more etheric oxygen atoms;

each occurrence of $Z^\theta$, which forms a cyclic structure with a silicon atom, is independently given by $—OG^5(OH)_{d-2}O—$, wherein $G^5$ is independently selected form the group consisting of a hydrocarbylene group of from 2 to 15 carbon atoms or a divalent heterocarbon of from 4 to 15 carbon atoms and containing one or more etheric oxygen atoms;

each occurrence of the subscripts, d, m, n, o, and p independently is an integer wherein d is from 2 to 6, more specifically 2 or 3 and still more specifically 2; m is from 0 to 20; n is specifically from 0 to 18; o is from 0 to 20; p is from 0 to 20; with the proviso that m+n+o+p is equal to or greater than 2.

In another embodiment herein there is provided an article of manufacture, such as the non-limiting examples selected from the group consisting of tires, industrial goods, shoe soles, hoses, seals, gaskets, and cable jackets, of which at least one component is the cured rubber composition of the herein described rubber compositions. In one embodiment, the silanes and/or silane mixtures herein offer a means for significantly reducing volatile organic compound (VOC) emissions during rubber manufacture, increase the dispersion of the filler within the rubber, and improving the coupling between the organic polymers and fillers.

In another embodiment herein the mercaptofunctional silane-based compositions herein are useful as coupling agents between elastomeric resins (i.e., rubbers) and fillers. In one embodiment, the mercaptofunctional silane compositions are unique in that the high efficiency of the mercaptan group can be utilized without the detrimental side effects typically associated with the use of mercaptosilanes, such as high processing viscosity, less than desirable filler dispersion, premature curing (scorch), and odor. In yet another embodiment, these benefits are obtained because the mercaptan group is part of a high boiling compound that liberates diol or higher polyhydroxy-containing compound upon use. In still another embodiment, during this non-productive mixing step, the cyclic and/or bridged alkoxysilyl groups can react with the filler. In one embodiment herein mercaptosilane composition, free-flowing filler composition and rubber composition can be cured as described herein and/or using procedures known to those skilled in the art.

In another specific embodiment herein, the mercaptofunctional silane-based compositions herein provide significant advantages over traditional coupling agents that have found extensive use in the rubber and tire industries. These traditional silanes usually contain in their molecular structures three alkoxy groups, e.g., ethoxy groups, on each silicon atom, which results in the release of up to three moles of simple monohydroxy alcohol, e.g., ethanol for each silane equivalent during the rubber manufacturing process in which the silane couples to the filler. The release of simple mono alcohols is a great disadvantage because they are flammable and therefore pose a threat of fire, and because they contribute so greatly to volatile organic compound (VOC) emissions and are therefore potentially harmful to the environment.

In one specific embodiment herein, utilizing any of the silanes and/or silane mixtures disclosed herein can result in VOC emission that is reduced. In one embodiment, VOC emission from a product/composition comprising the silanes or silanes mixtures disclosed herein can be less than the VOC emission in an equivalent product/composition that does not contain said silanes or silanes mixtures disclosed herein. In yet a further embodiment, reduced VOC emission can comprise specifically less than about 30 weight percent of the weight of the mercaptofunctional silane, more specifically less than about 10 weight percent of the mercaptofunctional silane and most specifically less than about 1 weight percent of the mercaptofunctional silane. In one embodiment, the VOC emission are reduced because the resulting byproducts of hydrolysis are $G^5(OH)_d$, $(HO)(CR^O_2)_fOH$ and $HO(CR^O_2CR^O_2O)_eOH$, are required to have a having a boiling point greater than 180° C. at atmospheric pressure.

In one embodiment herein, the mercaptofunctional silane-based compositions described herein eliminate or greatly mitigate the foregoing problems by reducing volatile monoalcohol emissions to only one, less than one, and even essentially zero, moles of monoalcohol per silane equivalent. In one specific embodiment, they accomplish this because the silane alkoxy groups are replaced with polyhydroxy alcohols, e.g., diol derived bridging groups, and thus such polyhydroxy alcohols are released during the rubber manufacture process in place of much, or nearly all, of the mono alcohol released. In yet a further specific embodiment, describing the advantages of the mercaptofunctional silanes herein with specific reference to those silanes that are prepared with diols (such advantages being realizable with polyhydroxy-containing compounds of higher hydroxyl functionality), e.g., having boiling points in excess of rubber processing temperatures, are not vaporized out of the rubber during the rubber manufacture process, as is the case, e.g., with ethanol, but are retained by the rubber where they migrate to the silica surface due to their high polarity and become hydrogen bonded to the surfaces of siliceous fillers such as silicas. In another embodiment, the presence of diols on silica surfaces leads to further advantages not obtainable with ethanol (due to its volatility and ejection during the rubber compounding process) in the subsequent cure process, in which such presence prevents the silica surface from binding the curatives and thereby interfering with the cure. Traditional silanes not based on diols require more curatives to counter losses due to silica binding.

In another embodiment, the addition of hydrocarbon-based diols or polyhydroxyl-containing compounds to the rubber compounding formulation prior to and/or concurrent with the addition of curatives is of advantage for the efficient utilization of the curatives, in particular, and polar substances, such as, but not limited to, amines, amides, sulfenamides, thiurams, and guanidines. In yet another embodiment, whether diols or the polyhydroxyl-containing compounds are exclusively added in the form of di- or polyhydroxyl-derived silanes or as free diols or polyhydroxyl-containing compounds in combination with the silane coupling agents, the polarity of the diols or polyhydroxyl-containing compounds is of advantage to the rubber compounding process. In one more embodiment, these polar substances tend to migrate to the filler surface due to dipole interactions with the filler; which tends to make them unavailable within the organic polymer matrix, where their functions include dispersion of the free flowing filler composition and acceleration, or retardation, of the curing reactions. In one embodiment, the hydrocarbon-based diols or polyhydroxyl-containing compounds enhance the function of the curatives by interfering with their tendency to bind to the silica surface thereby forcing them into the rubber matrix to perform their function. In another embodiment herein, the hydrocarbon-based diols or polyhydroxyl-containing compounds accomplish this by themselves being very polar, and thereby by themselves binding to the filler surface, leaving less room for the curatives to bind to filler. In a further specific embodiment, the hydrocarbon-based diols thus act as curative displacing agents from the filler. In yet another specific embodiment, the short chain of the hydrocarbon-based diols or polyhydroxyl-containing compounds further enhances their function by a chelate effect. In one embodiment, the number of carbon atoms between the dialkoxide groups of $Z^\theta$ and/or $Z^\beta$ herein are important and are defined by the divalent radical —$O(R^OCR^O)_f$ O— and $[—O(R^OCR^O)_fO—]_{0.5}$, respectively, wherein each occurrence of $f$ is 2 or 3. In a more specific embodiment, these chains of two or three carbon atoms between the two OH groups of the diol promote the formation of 5- or 6-membered rings when both oxygen atoms bind to a common silicon atom of the silanes of Formulae (1). In an even more specific embodiment, this dual binding to a common center, known, and referred to herein as the chelate effect, increases the amount of cyclic dialkoxysilyl group and inhibits the formation of gel. In a further specific embodiment, after reactions with the silica in the rubber-compounding step, the diols that have been released have a high affinity to the filler because they can chelate with the metal or silicon atom on the filler surface thereby enhancing their ability to prevent the binding of the curatives to the filler. In a further specific embodiment an important advantage of the silanes and/or silane mixtures described herein is that the byproducts of the silane coupling process are themselves of utility in enhancing the rubber compounding process, the value of the resulting rubber compositions, and/or any articles of manufacture employing the rubber compositions. In one embodiment, thus, the mercaptosilanes containing a bridging and/or cyclic dialkoxy group enhance the ease and completeness of filler dispersion and retarding the reversal of this process, namely, filler reagglomeration.

In one embodiment herein there is provided a rubber composition comprising (a) at least one rubber component, (b) at least one particulate filler and (c) at least one mercaptofunctional silane as described herein.

In one embodiment, an important advantage of the silanes described herein is that the by-products of the silane coupling process are themselves of utility in enhancing the rubber compounding process, the value of the resulting rubber compositions, and/or any articles of manufacture employing the rubber compositions.

In one embodiment, at least one of the mercaptofunctional silane coupling agents that contain cyclic and/or bridging dialkoxysilyl groups is mixed with the organic polymer before, during, or after the compounding of the filler into the organic polymer. In one embodiment, the silanes are added before or during the compounding of the filler into the organic polymer because these silanes facilitate and improve the dispersion of the filler. In a more specific embodiment, the total amount of silane present in the resulting rubber composition should be about 0.05 to about 25 parts by weight per hundred parts by weight of organic polymer (phr). In another embodiment, the amount of mercaptofunctional silane present in the free flowing filler composition is from about 0.1 to about 70 weight percent based on total weight of free flowing filler composition. In yet another embodiment, the amount of mercaptofunctional silane present in the free flowing filler composition is from about 0.5 to about 20 weight percent based on total weight of free flowing filler composition. In one other embodiment the amount of filler in the free flowing filler composition is from about 99.9 to about 30 weight percent based on total weight of free flowing filler composition. In yet one other embodiment the amount of filler in the free flowing filler composition is from about 99.5 to about 80 weight percent based on total weight of free flowing filler composition. In another embodiment, the amount of silane present in the rubber is from about 0.2 to 10 phr. In yet another embodiment, the amount of silane present in the rubber is from about 3 to 8 phr. In one embodiment, fillers can be used in quantities ranging specifically from about 5 to about 100 phr, more specifically from about 25 to about 80 phr and most specifically from about 50 to about 70 phr.

In one embodiment, in practice, sulfur vulcanized rubber products typically are prepared by thermomechanically mixing rubber and various ingredients in a sequentially step-wise manner followed by shaping and curing the compounded rubber to form a vulcanized product. In a more specific embodiment, first, for the aforesaid mixing of the rubber and various ingredients, typically exclusive of sulfur and sulfur vulcanization accelerators (collectively "curing agents"), the rubber(s) and various rubber compounding ingredients are usually blended in at least one, and optionally (in the case of silica filled low rolling resistance tires) two or more, preparatory thermomechanical mixing stage(s) in suitable mixers. In a further embodiment, such preparatory mixing is referred to as non-productive mixing or non-productive mixing steps or stages. In a more specific embodiment, such preparatory mixing usually is conducted at temperatures in specifically in the range of from about 140° C. to about 180° C., and more specifically in the range of from about 150° C. to about 160° C.

In one embodiment, subsequent to such preparatory mix stages, in a final mixing stage, sometimes referred to as a productive mix stage, curing agents, and possibly one or more additional ingredients, are mixed with the rubber compound or composition, typically at a temperature in a range of 50° C. to 130° C., which is a lower temperature than those utilized in the preparatory mix stages to prevent or retard premature curing of the sulfur curable rubber, which is sometimes referred to as scorching of the rubber composition.

In another embodiment, the rubber mixture, sometimes referred to as a rubber compound or composition, typically is allowed to cool, sometimes after or during a process of intermediate mill mixing, between the aforesaid various mixing steps, for example, to a temperature of about 50° C. or lower.

In another embodiment herein, when it is desired to mold and to cure the rubber, the rubber is placed into the appropriate mold and heated to about at least 130° C. and up to about 200° C., which will cause the vulcanization of the rubber by the mercapto groups on the mercaptosilane and any other free sulfur sources in the rubber mixture.

In one embodiment, by thermomechanical mixing, it is meant that the rubber compound, or composition of rubber and rubber compounding ingredients, is mixed in a rubber mixture under high shear conditions where it autogenously heats up as a result of the mixing, primarily due to shear and associated friction within the rubber mixture in the rubber mixer. In one embodiment, several chemical reactions can occur at various steps in the mixing and curing processes.

In one embodiment, the first reaction is a relatively fast reaction and is considered herein to take place between the filler and the alkoxysilyl group of the cyclic and/or bridging dialkoxy mercaptofunctional silanes, —SiX where X is a hydrolysable group, —SiZ$^\beta$ or SiZ$^\theta$, herein. In a further embodiment, such reaction can occur at a relatively low temperature, such as, for example, about 120° C. In a further embodiment, the second reaction is considered herein to be the reaction which takes place between the sulfur-containing portion of the silane, and the sulfur vulcanizable rubber at a higher temperature; for example, above about 140° C.

In one embodiment, another sulfur source can be used, for example, in the form of elemental sulfur as $S_8$. In a more specific embodiment, a sulfur donor is considered herein as a sulfur-containing compound that liberates free, or elemental sulfur, at a temperature in a range of about 140° C. to about 190° C. In an even more specific embodiment, such sulfur donors can be those such as the non-limiting examples of polysulfide vulcanization accelerators with at least two connecting sulfur atoms in their polysulfide bridge. In an even yet more specific embodiment, the amount of free sulfur source addition to the mixture can be controlled or manipulated as a matter of choice relatively independently from the addition of the aforesaid cyclic and/or bridging dialkoxy mercaptofunctional silane composition.

Thus, in one embodiment for example, the independent addition of a sulfur source can be manipulated by the amount of addition thereof and by sequence of addition relative to addition of other ingredients to the rubber mixture.

In another embodiment herein, a rubber composition is prepared by a process comprising the sequential steps of:
a) thermomechanically mixing, in at least one preparatory mixing operation, to a temperature of from about 140° C. to about 180° C., for a total mixing time of from about 1 to about 20 minutes for such mixing operation(s):
 i) about 100 parts by weight of at least one sulfur vulcanizable rubber selected from the group consisting of conjugated diene homopolymers and copolymers and copolymers of at least one conjugated diene and aromatic vinyl compound,
 ii) from about 5 to about 100 parts by weight of particulate filler, wherein the filler preferably contains from 0 to about 85 weight percent carbon black, and
 iii) from about 0.05 to about 20 parts by weight filler of at least one mercaptofunctional silane of Formula (1) of claim 1;
b) blending the mixture from step (a), in a final thermomechanical mixing step at a temperature of from about 50° C. to about 130° C. for a time sufficient to blend the rubber, and a curing agent at 0 to 5 parts by weight; and,
(c) optionally curing said mixture at a temperature in the range of from about 130 to about 200° C. for a period of from about 5 to about 60 minutes.

Suitable rubber component (a) (organic polymers) and fillers are well known in the art and are described in numerous texts, of which two examples include The Vanderbilt Rubber Handbook; R. F. Ohm, ed.; R.T. Vanderbilt Company, Inc., Norwalk, Conn.; 1990 and Manual For The Rubber Industry; T. Kempermann, S. Koch, J. Sumner, eds.; Bayer A G, Leverkusen, Germany; 1993. In yet an even further embodiment, some representative non-limiting examples of suitable rubber component (a) (organic polymers) include solution styrene-butadiene rubber (SSBR), emulsion styrene-butadiene rubber (ESBR), natural rubber (NR), polybutadiene (BR), ethylene-propylene terpolymers (EPDM), and acrylonitrile-butadiene rubber (NBR).

In one embodiment herein, the rubber composition component (a) is comprised of at least one diene-based elastomer, or rubber. In an even more specific embodiment, suitable monomers for preparing the rubbers are conjugated dienes which are those such as the non-limiting examples of isoprene and 1,3-butadiene; and suitable vinyl aromatic compounds which are those such as the non-limiting examples of styrene and alpha methyl styrene; and combinations thereof. Thus in a more specific embodiment, the rubber is a sulfur curable rubber. In a further embodiment, such diene based elastomer, or rubber, can be selected, from the non-limiting examples of at least one of cis-1,4-polyisoprene rubber (natural and/or synthetic), and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35-50 percent vinyl), high vinyl polybutadiene rubber (50-75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (ESBR) is also contemplated as diene based rubbers for use herein such as those having a relatively conventional styrene content of 20 to 28 percent bound styrene or, for some applications, an ESBR having a medium to relatively high bound styrene content, namely, a bound styrene content of 30 to 45 percent. In an even further specific embodiment, emulsion polymerization prepared styrene/butadiene/acrylonitrile terpolymer rubbers containing 2 to 40 weight percent bound acrylonitrile in the terpolymer are also contemplated as diene based rubbers for use herein.

In another embodiment herein, the solution polymerization prepared SBR (SSBR) typically has a bound styrene content in a range of specifically from about 5 to about 50, more specifically from about 9 to about 36, and most specifically of from about 20 to about 30 weight percent. In a more specific embodiment, polybutadiene elastomer can he conveniently characterized, for example, by having at least a 90 weight percent cis-1,4-content.

In one embodiment some representative non-limiting examples of suitable filler materials include include metal oxides, such as silica (pyrogenic and precipitated), titanium dioxide, aluminosilicate, and alumina, siliceous materials, including clays and talc, and carbon black. In a more specific embodiment, particulate, precipitated silica is also sometimes used for such purpose, particularly in connection with a silane. In one embodiment wherein the filler is a silica alone or in combination with one or more other fillers. In another specific embodiment in some cases, a combination of silica and carbon black is utilized for reinforcing fillers for various rubber products, including treads for tires. In one embodiment, alumina can be used either alone or in combination with silica. The term "alumina" can be described herein as aluminum oxide, or $Al_2O_3$. In a further specific embodiment, the fillers can be hydrated or in anhydrous form. Use of alumina in rubber compositions is known, see, for example, U.S. Pat. No. 5,116,886 and EP 631 982, the contents of which are incorporated by reference herein.

In one embodiment there is provided herein a process for preparing a rubber composition comprising adding to a rubber composition reaction-forming mixture, such as a mixture of the herein described rubber composition components (a), (b) and (c) in an effective amount of at least one mercaptofunctional silane composition as described herein. In one embodiment an effective amount of mercaptofunctional silane composition, in a rubber composition reaction forming mixture, as described herein, is specifically of from about 0.2 to about 20, more specifically of from about 0.5 to about 15 and most specifically of from about 2 to about 10 weight percent of mercaptofunctional silane based on the total weight of rubber composition reaction forming mixture. In another embodiment, reaction-forming mixture further comprises a filler as described herein and in an amount of specifically of from about 2 to about 70, more specifically of from about 5 to about 50 and most specifically of from about 20 to about 40 weight percent of filler, based on the total weight of rubber composition reaction-forming mixture. In yet another embodiment reaction-forming mixture can even further comprise a rubber component (a) described herein, and in an amount of specifically of from about 30 to about 98, more specifically of from about 50 to about 95 and most specifically of from about 60 to about 80 weight percent of rubber component based on the total weight of rubber composition reaction forming mixture. In one embodiment herein, rubber composition as described herein can have amounts of components (a), (b) and (c) as described for rubber component reaction forming mixture.

In one embodiment, the mercaptofunctional silane compositions that contain cyclic and/or bridging dialkoxysilyl groups can be premixed, or pre-reacted, with the filler particles or added to the rubber mix during the rubber and filler processing, or mixing stage. In another embodiment, if the silane and filler are added separately to the rubber mix during the rubber and filler mixing, or processing stage, it is considered that the organofunctional silane compositions that contain cyclic and/or bridging dialkoxysilyl groups then couple in situ to the filler.

In one embodiment herein, vulcanized rubber composition should contain a sufficient amount of filler to contribute a reasonably high modulus and high resistance to tear. In a specific embodiment, the combined weight of the filler can be as low as about 5 to about 100 phr, but is more specifically of from about 25 to about 85 phr, and most specifically of from about 50 to about 70 phr.

In one embodiment the term "filler" as used herein means a substance that is added to the elastomer to either extend the elastomer or to reinforce the elastomeric network. Reinforcing fillers are materials whose moduli are higher than the organic polymer of the elastomeric composition and are capable of absorbing stress from the organic polymer when the elastomer is strained. In one embodiment fillers included fibers, particulates, and sheet-like structures and can be composed of inorganic minerals, silicates, silica, clays, ceramics, carbon, organic polymers, diatomaceous earth. In one embodiment the filler herein can be essentially inert to the silane with which it is admixed, or it can be reactive therewith.

In one embodiment the term "particulate filler" as used herein means a particle or grouping of particles to form aggregates or agglomerates. In one embodiment the particulate filler herein can be essentially inert to the silane with which it is admixed, or it can be reactive therewith.

In one embodiment the term "carrier" as used herein means a porous or high surface area filler or organic polymer that has a high adsorption or absorption capability and is capable of carrying up to 75 percent liquid silane while maintaining its free-flowing and dry properties. In one embodiment the carrier filler or carrier polymer herein is essentially inert to the silane and is capable of releasing or deabsorbing the liquid silane when added to the elastomeric composition.

In an embodiment, fillers of the present invention can be used as carriers for liquid silanes and reinforcing fillers for elastomers in which the mercapto functional silane, and more specifically, the mercaptofunctional silane (1) is capable of reacting or bonding with the surface. In one embodiment, the fillers that are used as carrier should be non-reactive with the mercaptosilane of this invention. In one embodiment the non-reactive nature of the fillers is demonstrated by ability of the merpcaptosilane to be extracted at greater than 50 percent of the loaded silane using an organic solvent. In one embodiment the extraction procedure is given in U.S. Pat. No. 6,005,027, which is incorporated herein by reference. In one embodiment, carriers include, but are not limited to, porous organic polymers, carbon black, diatomaceous earth, and silicas that characterized by relatively low differential of less than 1.3 between the infrared absorbance at 3502 $cm^{-2}$ of the silica when taken at 105° C. and when taken at 500° C., as described in U.S. Pat. No. 6,005,027. In one embodiment, the amount of mercapto functional silane that can be loaded on the carrier is between 0.1 and 70 percent. In another embodiment, the mercpato functional silane is load on the carrier at concentrations between 10 and 50 percent. In yet another embodiment, the filler is a particulate filler.

In one embodiment herein reinforcing fillers useful herein include fillers in which the silanes are reactive with the surface of the filler. In one embodiment some representative examples of the fillers include, but are not limited to, inorganic fillers, siliceous fillers, metal oxides such as silica (pyrogenic and/or precipitated), titanium, aluminosilicate and alumina, clays and talc, and the like. In one embodiment herein, particulate, precipitated silica is useful for such purpose, particularly when the silica has reactive surface silanols. In one embodiment of the present invention, a combination of 0.1 to 20 percent of mercapto functional silane, and more specifically, the mercapto functional silanes (1) and 80 to 99.9 percent silica or other reinforcing fillers is utilized to reinforce various rubber products, including treads for tires. In another embodiment, a filler is comprising from about 0.5 to about 10 percent mercaptofunctional silane, and more specifically, mercapto functional silane (1) and about 90 to about 99.5 weight percent particulate filler. In another embodiment herein, alumina can be used alone with the mercapto functional silane, and more specifically, mercaptofunctional silane (1) or in combination with silica and the mercapto functional silane. In one embodiment herein the term, alumina, can be described herein as aluminum oxide, or $Al_2O_3$. In a further embodiment herein, the fillers may be in the hydrated form.

In one embodiment the filler can be essentially inert to the silane with which it is admixed as is the case with carbon black or organic polymers, or it can be reactive therewith, e.g., the case with carriers possessing metal hydroxyl surface functionality, e.g., silicas and other siliceous particulates which possess surface silanol functionality.

In one embodiment herein, precipitated silica is utilized as filler. In a more specific embodiment, the silica filler herein can as characterized by having a BET surface area, as measured using nitrogen gas, specifically in the range of from about 40 to about 600 $m^2/g$, and more specifically in a range of from about 50 to about 300 $m^2/g$ and most specifically in a range of from about 100 to about 150 $m^2/g$. In another specific embodiment, the BET method of measuring surface area is described in the Journal of the American Chemical Society, Volume 60, page 304 (1930), which is the method used herein. In yet another specific embodiment, the silica typically can also be characterized by having a dibutylphthalate (DBP) absorption value in a range of specifically from about 100 to about 350, more specifically from about 150 to about 300 and most specifically from about 200 to about 250. In an even further specific embodiment, further, useful silica fillers, as well as the aforesaid alumina and aluminosilicate fillers, can be expected to have a CTAB surface area in a range of from about 100 to about 220 $m^2/g$. In an even further specific embodiment, the CTAB surface area is the external surface area as evaluated by cetyl trimethylammonium bromide with a pH of 9; the method is described in ASTM D 3849.

Mercury porosity surface area is the specific surface area determined by mercury porosimetry. In this technique, mercury is penetrated into the pores of the sample after a thermal treatment to remove volatiles. In a more specific embodiment, set-up conditions can be suitably described as using a 100 mg sample; removing volatiles during 2 hours at 105° C. and ambient atmospheric pressure; and ambient to 2000 bars pressure measuring range. In another more specific embodiment, such evaluation can be performed according to the method described in Winslow, et al. in ASTM bulletin, p. 39 (1959) or according to DIN 66133; for such an evaluation, a CARLO-ERBA Porosimeter 2000 can be used. In one embodiment, the average mercury porosity specific surface area for the selected silica filler should be in a range of specifically from about 100 to about 300 $m^2/g$, more specifically from about 150 to about 275 m²/g, and most specifically from about 200 to about 250 m²/g.

In one embodiment, a suitable pore size distribution for the silica, alumina and aluminosilicate according to such mercury porosity evaluation is considered herein to be: five percent or less of its pores having a diameter of less than about 10 nm; from about 60 to about 90 percent of its pores have a diameter of from about 10 to about 100 nm; from 10 to about 30 percent of its pores having a diameter of from about 100 to about 1,000 nm; and from about 5 to about 20 percent of its pores have a diameter of greater than about 1,000 nm. In a second embodiment, the silica can be expected to have an average ultimate particle size, for example, in the range of from about 0.01 to about 0.05 µm as determined by electron microscopy, although the silica particles can be even smaller, or possibly larger, in size. In one embodiment, various commercially available silicas can be considered for use herein such as, those available from PPG Industries under the HI-SIL trademark, in particular, HI-SIL 210, and 243; silicas available from Rhone-Poulenc, e.g., ZEOSIL 1165 MP; silicas available from Degussa, e.g., VN2 and VN3, etc. and silicas available from Huber, e.g., HUBERSIL 8745.

In one embodiment, where it is desired for rubber composition, which contains both a siliceous filler such as silica, alumina and/or aluminosilicates and also carbon black reinforcing pigments, to be primarily reinforced with silica as the reinforcing pigment, it is often more specific that the weight ratio of such siliceous fillers to carbon black is at least 3/1 and preferably at least 10/1 and, thus, in a range of 3/1 to 30/1. In a more specific embodiment, the filler can comprise from about 15 to about 95 weight percent precipitated silica, alumina and/or aluminosilicate and, correspondingly from about 5 to about 85 weight percent carbon black, wherein the said carbon black has a CTAB value in a range of from about 80 to about 150. In one specific embodiment, alternatively, the filler can comprise from about 60 to about 95 weight percent of said silica, alumina and/or aluminosilicate and, correspondingly, from about 40 to about 5 weight percent of carbon black. In another specific embodiment, the siliceous filler and carbon black can be pre-blended or blended together in the manufacture of the vulcanized rubber.

In one embodiment, the rubber composition herein can be compounded by methods known in the rubber compounding art, such as mixing the various sulfur-vulcanizable constituent rubbers with various commonly used additive materials as, for example, curing aids such as sulfinur, activators, retarders and accelerators, processing additives such as oils, resins e.g., tackifying resins, silicas, plasticizers, fillers, pigments, fatty acid, zinc oxide, waxes, antioxidants and antiozonants, peptizing agents, and reinforcing materials such as, for example, carbon black, and the like. In another specific embodiment, depending on the intended use of the sulfur vulcanizable and sulfur vulcanized material (rubbers), the additives mentioned herein are selected and commonly used in conventional amounts.

In one embodiment, the vulcanization can be conducted in the presence of an additional sulfur vulcanizing agent. In one specific embodiment, some non-limiting examples of suitable sulfur vulcanizing agents include, e.g., elemental sulfur (free sulfur) or sulfur donating vulcanizing agents, such as the non-limiting examples of, an amino disulfide, polymeric polysulfide or sulfur olefin adducts, which are conventionally added in the final, productive, rubber composition mixing step. In another specific embodiment, the sulfur vulcanizing agents (which are common in the art) are used, or added in the productive mixing stage, in an amount ranging from about 0.4 to about 3 phr, or even, in some circumstances, up to about 8 phr, with a range of from about 1.5 to about 2.5 phr, and in some cases from about 2 to about 2.5 phr, being most specific.

In one embodiment, vulcanization accelerators, i.e., additional sulfur donors, can also be used. In one embodiment, it will be appreciated that they can be those such as the non-limiting examples of benzothiazole, alkyl thiuram disulfide, guanidine derivatives, and thiocarbamates. In another specific example, representative of such accelerators are, e.g., but not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamyl-sulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine), dithiobis (dibenzyl amine) and combinations thereof. In another specific embodiment, other additional sulfur donors, include, e.g., thiuram and morpholine derivatives. In a more specific embodiment, representative of such donors include, e.g., but are not limited to, dimorpholine disulfide, dimorpholine tetrasulfide, tetramethyl thiuram tetrasulfide, benzothiazyl-2,N-dithiomorpholide, thioplasts, dipentamethylenethiuram hexasulfide, disulfidecaprolactam and combinations thereof.

In one embodiment, accelerators are used to control the time and/or temperature required for vulcanization and to improve the properties of the vulcanizate. In one embodiment, a single accelerator system can be used, i.e., a primary accelerator. In another embodiment, conventionally and more specifically, a primary accelerator(s) is used in total amounts ranging from about 0.5 to about 4, preferably from about 0.8 to about 1.5 phr. In a more specific embodiment, combinations of a primary and a secondary accelerator can be used with the secondary accelerator being used in smaller amounts (e.g., from about 0.05 to about 3 phr) in order to activate and to improve the properties of the vulcanizate. In yet a further embodiment, delayed action accelerators can also be used. In yet an even further embodiment, vulcanization retarders can also be used. In one embodiment, suitable types of accelerators are those such as the non-limiting examples of amines, disulfides, guanidines, thioureas, thiazoles, thiurams, sulfenamides, dithiocarbamates, xanthates and combinations thereof. In a more specific embodiment, the primary accelerator is a sulfenamide. In another specific embodiment, if a second accelerator is used, the secondary accelerator is more specifically a guanidine, dithiocarbamate or thiuram compound.

In one embodiment some non-limiting amounts of tackifier resins, if used, can be from about 0.5 to about 10 phr, usually from about 1 to about 5 phr. In one specific embodiment, typical amounts of processing aids comprise from about 1 to about 50 phr. In another specific embodiment, such processing aids can include, the non-limiting examples of aromatic, naphthenic and/or paraffinic processing oils, and combinations thereof. In one more specific embodiment, typical amounts of antioxidants are from about 1 to about 5 phr. In one other specific embodiment, representative antioxidants include, the non-limiting examples of diphenyl-p-phenylenediamine and others, e.g., those disclosed in the *Vanderbilt Rubber Handbook* (1978), pages 344-346. In yet another embodiment, typical amounts of antiozonants, are from about 1 to about 5 phr. In one more embodiment, typical amounts of fatty acids, if used, which can include the non-limiting example of stearic acid, are from about 0.5 to about 3 phr. In one more embodiment, typical amounts of zinc oxide are from about 2 to about 5 phr. In yet another specifice embodiment, typical amounts of waxes are from about 1 to about 5 phr. In one embodiment, often microcrystalline waxes are used. In another embodiment, typical amounts of peptizers are from about 0.1 to about 1 phr. In yet a further embodiment, typical peptizers include, the non-limiting examples of pentachlorothiophenol, dibenzamidodiphenyl disulfide and combinations thereof.

In one embodiment herein, rubber compositions herein can be used for various purposes. In one specific embodiment, for example, they can be used for the non-limiting examples of various tire compounds, shoe soles, hoses, cable jackets, gaskets, and other industrial goods. In a more specific embodiment, such articles can be built, shaped, molded and cured by various known and conventional methods as is readily apparent to those skilled in the art. In one even more specific embodiment, one particularly useful application of the rubber compositions herein is for the manufacture of tire treads. In one embodiment, an advantage of tires, tire treads, or other articles of manufacture derived from the rubber compositions herein is that they suffer from less VOC emissions during their lifetime and use as a result of having been manufactured from a rubber compound that contains less residual silane ethoxy groups than do rubber compounds of the known and currently practiced art. In a more specific embodiment, this is a direct result of having used dialkoxy-functional silane coupling agents in their manufacture, which contain fewer or essentially no ethoxy groups on silicon, relative to the blends of mercaptosilane coupling agents of the currently known and practiced art. In one embodiment, the lack or reduction of ethoxysilane groups in the coupling agents used results in fewer residual ethoxy groups on silicon after the article of manufacture is produced, from which less or no ethanol can be released by hydrolysis of the residual ethoxysilane groups by exposure of the article of manufacture to water during use.

All references cited herein are incorporated by reference herein in their entirety.

The invention can be better understood by reference to the following examples in which the parts and percentages are by weight unless otherwise indicated.

EXAMPLE 1

3-Mercaptopropyltriethoxysilane (obtained from General Electric under the trade name Silquest A-1891, 514.3 grams, 2.16 mole), and 2-methyl-1,3-propanediol (purchased from Aldrich, 194.4 grams, 2.16 moles) were charged into a 1-liter round-bottomed flask equipped with a magnetic stirrer, short path condenser and receiver flask. Purolite (purchased from Rohm & Haas, 3.5 grams) was added to the reaction flask and the mixture was heated to 50° C. under a vacuum of initially 60 torr to about 1 torr for about 3 hours. Ethanol (185 grams, 4.02 moles) was collected. The reaction product was pressured filtered through a 3.5-micron pad. The weight of the product collected was 501.7 grams. GC/MS found a complex mixture that contained 3-({3-[2-mercapto-propyl)-5-methyl-[1,3,2]doxasilinan-2-yloxy]-2-methyl-propyl}-diethoxy-silyanyl)-propane-1-thiol and 3-2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propane-1-thiol.

EXAMPLE 2

3-Mercaptopropyltriethoxysilane (obtained from General Electric under the trade name Silquest A-1891, 438.8 grams, 1.84 mole), and 2-methyl-1,3-propanediol (purchased from Aldrich, 331.7 grams, 3.68 moles) were charged into a 1-liter round-bottomed flask equipped with a magnetic stirrer, short path condenser and receiver flask. Sulfuric acid (0.39 gram) was added to the reaction flask and the mixture was heated to 50° C. under a vacuum of initially 40 torr to about 1 torr (full vaccum) 3.5 hours. Ethanol (263 grams, 5.71 moles) was collected. The reaction product was then neutralized with 1.44 grams of 21% sodium ethoxy in ethanol and then stripped 1.5 hours. The weight of the product collected was 485.6 grams. GC analysis found a complex mixture that contained 3-({3-[2-mercapto-propyl)-5-methyl-[1,3,2]dioxasilinan-2-yloxy]-2-methyl-propyl}-diethoxy-silyanyl)-propane-1-thiol and higher molecular weight components.

EXAMPLE 3

3-Mercaptopropyltriethoxysilane (obtained from General Electric under the trade name Silquest A-1891, 720.5 grams, 3.02 mole), and 2-methyl-1,3-propanediol (purchased from Aldrich, 817.0 grams, 9.07 moles) were charged into a 3-liter round-bottomed flask equipped with a magnetic stirrer, short path condenser and receiver flask. Sulfuric acid (0.78 gram) was added to the reaction flask and the mixture was heated to about 50° C. under a vacuum of initially 30 torr to about 10 torr for 3.5 hours. Ethanol (389.4 grams, 8.5 moles) was collected. The reaction product was then neutralized with 2.5 grams of 21% sodium ethoxy in ethanol and then stripped 1 hour. The weight of the product collected was 1108.9 grams.

EXAMPLE 4

3-Mercaptopropyltriethoxysilane (100 grams, 0.42 mole), and 2-methyl-2,4-pentanediol (50 grams, 0.42 mole) are charged into a 1-liter round-bottomed flask equipped with a magnetic stirrer, short path condenser and receiver flask. Titanium isopropoxide (0.85 gram) is added to the reaction flask and the mixture is heated to 70° C. under a vacuum of initially about 370 torr for 1 hour. 2-Methyl-1,3-propanediol (18.9 grams, 0.21 mole) is added and heated.

COMPARATIVE EXAMPLES 5 AND 6 AND EXAMPLES 7, 8, 9 AND 10

Cured rubber compositions in the form of plaques were prepared and their physical and dynamic properties measured to determine effect of loading.

A typical silica-rubber SBR formulation was used as described below in Table 1. Mixing was carried out in a 1.7-liter Banbury tangential mixer.

TABLE 1

| Silica-Silane/Rubber Formulation | |
|---|---|
| PHR | Components |
| 103.2 | sSBR (Buna VSL 5025-1 from Bayer AG) |
| 25 | BR (Budene 1207 from Goodyear) |
| 80 | silica (Zeosil 1165MP from Rhodia) |
| 3.0 | carbon black (N-330) |
| Variable | silane |
| 4.5 | oil (Sundex 8125 from Sun Oil) |
| 2.5 | zinc oxide (Kadox 720C from ZincCorp.) |
| 1.0 | stearic acid (Industrene R from Witco, Crompton) |
| 2.0 | 6 PPD (Flexzone 7P from Uniroyal, Crompton) |
| 1.5 | Wax (Sunproof Improved from Uniroyal, Crompton) |
| Final Mix Ingredients | |
| 1.4 | sulfur (Rubbermakers Sulfur 104 from Harwick) |
| 1.7 | CBS (Delac S from Uniroyal, Crompton) |
| 2.0 | DPG (from Uniroyal, Crompton) |

The procedure which was used for preparing a single non-productive mix is presented in Table 2 below.

TABLE 2

One Pass Procedure; Cooling with water @ 25° C., 68% fill factor:

| Step | Procedure |
|---|---|
| 1 | Add polymers, RDM (ram down mix) 30 seconds |
| 2 | Add 50% silica, all silane, RDM 30 seconds |
| 3 | Add remaining 50% silica, oil, RDM 30 seconds |
| 4 | Dust down, RDM 20 seconds |
| 5 | Add ZnO, steric acid, Flexzone 7P, wax and carbon black, RDM 60 seconds |
| 6 | Dust down, RDM to 170° C. (in approx. 2 minutes) by increasing rotor speed |
| 7 | Hold at 170° C. for 8 minutes by changing speeds on the mixer. |
| 8 | Dump, sheet off roll mill @ 65-70° C. to cool |

The procedure for preparing a single productive mix involved adding sulfur and accelerators (primary and secondary) into a masterbatch prepared as described in Table 2 on a two-roll mill at 65 to 70° C. After all the silica filler, silane and oil were incorporated into a given mix, the rpm of the rotors was raised so as to achieve the desired silanization temperature. The mix was then held at that temperature for 8 minutes. The mix procedures are shown in Table 2, above.

Curing and testing of the cured rubber compositions in the form of plaques were carried out according to ASTM standards. In addition, small strain dynamic tests were carried out on a Rheometrics Dynamic Analyzer (ARES-Rheometrics Inc.). The specific curing procedure, measurements and measuring procedures were as follows:

| Curing Procedure/Measurement | Testing Standard |
|---|---|
| Mooney viscosity and scorch | ASTM D1646 |
| Oscillating disc rheometry | ASTM D2084 |
| Curing of test plaques | ASTM D3182 |
| Stress-strain properties | ASTM D412 |
| Heat build-up | ASTM D623 |

Dynamic Mechanical Properties:

Payne effect strain sweeps were carried out from dynamic strain amplitudes of 0.01% to about 25% shear strain amplitude at 10 Hz and 60° C. The dynamic parameters, $G'_{initial}$, $\Delta G'$, $G''_{max}$, $\tan \delta_{max}$ were extracted from the non-linear responses of the rubber compounds at small strains. In some cases, steady state values of tan δ were measured after 15 minutes of dynamic oscillations at strain amplitudes of 35% (at 60° C.). Temperature dependence of dynamic properties were also measured from about −80° C. to +80° C. at small strain amplitudes (1 or 2%) at a frequency of 10 Hz. The rheological, physical and dynamic properties of the rubber compounds, Comparative Examples 5 and 6 (silane is Silquest A-1891 silane) and Example 7, 8, 9 and 10 (silane from Example 3) are given in Table 3.

TABLE 3

The rheological, physical and dynamic properties of rubber

| | Example No. | | | | | |
|---|---|---|---|---|---|---|
| | Comp. 5 | Comp. 6 | 7 | 8 | 9 | 10 |
| Silane loading phr | 4 | 6.5 | 2 | 3 | 4 | 6.5 |
| Mooney Properties | | | | | | |
| Viscosity at 100° C. (ML1 + 4) | 89.52 | 78.77 | 73.6 | 70.94 | 80.58 | 74.3 |
| MV at 135° C. (MS1+) | 41.62 | 53.77 | 31.56 | 29.46 | 35.61 | 41.48 |
| Scorch at 135° C. (MS1 + $t_3$) (min) | 6.2 | 3.18 | 10.26 | 8.22 | 7.21 | 4.11 |
| Cure at 135° C. (MS1 + $t_{18}$) (min) | 9.28 | 4 | 14.1 | 12.17 | 10.34 | 5.1 |
| Rheometer (ODR) Properties, (1° arc at 149° C.) | | | | | | |
| $M_L$ (dN-m) | 15.79 | 13.93 | 12.14 | 10.67 | 12.81 | 12.71 |
| $M_H$ (dN-m) (30 min. timer) | 33.63 | 35.09 | 32.51 | 31.31 | 34.86 | 33.69 |
| t90 (min) (30 min. timer) | 18.52 | 19.35 | 17.79 | 15.42 | 13.13 | 5.97 |
| $t_{s1}$ (min) | 3.67 | 1.83 | 4.38 | 4.71 | 4.25 | 2.92 |
| $M_H − M_L$ | 17.84 | 21.16 | 20.38 | 20.64 | 22.05 | 20.98 |
| Physical Properties, (cured t90 at 149° C.) | | | | | | |
| Hardness (Shore A) | 56.3 | 58.3 | 59 | 56.3 | 57.7 | 57.7 |
| Tensile (MPa) | 15.10 | 12.26 | 19.76 | 19.44 | 18.56 | 15.54 |
| Elongation (%) | 312 | 250 | 492 | 414 | 354 | 306 |
| 25% Modulus (MPa) | 0.73 | 0.84 | 0.83 | 0.76 | 0.76 | 0.90 |
| 100% Modulus (MPa) | 2.05 | 2.50 | 1.63 | 1.73 | 2.01 | 2.35 |
| 300% Modulus (MPa) | 14.14 | "—" | 8.71 | 11.36 | 14.21 | 13.97 |
| Reinforcement Index, (300%/25%) | 19.37 | "—" | 10.46 | 14.94 | 18.70 | 15.51 |
| Reinforcement Index, (300%/100%) | 6.91 | "—" | 5.34 | 6.55 | 7.07 | 5.95 |
| Abrasion Loss (DIN) (mm³) | 107 | 118 | 133 | 115 | 108 | 114 |
| Dynamic Properties, (cured t90 at 149° C.) | | | | | | |
| Non-linearity (0- 10%) 60° C. | | | | | | |
| $G'_{initial}$ (MPa) | 2.39 | 2.47 | 3.89 | 2.27 | 2.98 | 2.16 |
| $\Delta G'$ (MPa) | 0.88 | 1.01 | 2.13 | 0.91 | 1.41 | 0.78 |
| $G''_{max}$ (MPa) | 0.30 | 0.30 | 0.55 | 0.28 | 0.34 | 0.23 |
| $\tan \delta_{max}$ | 0.16 | 0.15 | 0.19 | 0.15 | 0.15 | 0.13 |
| Temperature Dependence | | | | | | |
| $\tan \delta$ 0° C. | 0.54 | 0.54 | 0.51 | 0.57 | 0.48 | 0.58 |

TABLE 3-continued

The rheological, physical and dynamic properties of rubber

| | Example No. | | | | | |
|---|---|---|---|---|---|---|
| | Comp. 5 | Comp. 6 | 7 | 8 | 9 | 10 |
| tan δ 60° C. | 0.14 | 0.14 | 0.17 | 0.14 | 0.14 | 0.12 |
| G' 0° C. (MPa) | 6.10 | 5.62 | 9.68 | 6.56 | 6.12 | 6.42 |
| G' 60° C. (MPa) | 1.86 | 1.91 | 2.59 | 1.71 | 2.02 | 1.74 |

EXAMPLES 11, 12, 13 AND 14

The rubber compounds were prepared according to the procedure described in Comparative Example 5. The fill factor was 72 percent, and two passes were used Example 11. The data shows the effect of non-productive mixing temperature on performance of the rubber. The data are presented in Table 4.

While the invention has been described with reference to a number of exemplary embodiments, it will be understood by those skilled in the art that various changes can be made and equivalents can be substituted for elements thereof without departing from the scope of the invention. In addition, many modifications can be made to adapt a particular situation or material to the teachings of the invention without departing from essential scope thereof. Therefore, it is intended that the

TABLE 4

The rheological, physical and dynamic properties of rubber

| | Example No | | | |
|---|---|---|---|---|
| | 11 | 12 | 13 | 14 |
| Silane loading phr | 3.7 | 4 | 4 | 4 |
| Temperature | 140 | 160 | 170 | 180 |
| Mooney Properties | | | | |
| Viscosity at 100° C. (ML1 + 4) | 101 | 75.13 | 80.58 | 78.35 |
| MV at 135° C. (MS1+) | 59 | 32.4 | 35.61 | 34.49 |
| Scorch at 135° C. (MS1 + t$_3$) (min) | 3.4 | 7.31 | 7.21 | 7.53 |
| Cure at 135° C. (MS1 + t$_{18}$) (min) | 4.1 | 10.42 | 10.34 | 11.12 |
| Rheometer (ODR) Properties, (1° arc at 149° C.) | | | | |
| M$_L$ (dN-m) | 16.0 | 12.49 | 12.81 | 12.95 |
| M$_H$ (dN-m) (30 min. timer) | 31.0 | 34.34 | 34.86 | 34.7 |
| t90 (min) (30 min. timer) | 5.1 | 10.87 | 13.13 | 11.64 |
| t$_{s1}$ (min) | 2.1 | 4.49 | 4.25 | 4.82 |
| M$_H$ − M$_L$ | 15.0 | 21.85 | 22.05 | 21.76 |
| Physical Properties, (cured t90 at 149° C.) | | | | |
| Hardness (Shore A) | 60 | 57.7 | 57.7 | 58.3 |
| Tensile (MPa) | 15.5 | 19.64 | 18.56 | 17.18 |
| Elongation (%) | 300 | 381 | 354 | 343 |
| 25% Modulus (MPa) | 0.87 | 0.72 | 0.76 | 0.76 |
| 100% Modulus (MPa) | 2.36 | 1.89 | 2.01 | 2.01 |
| 300% Modulus (MPa) | 15.1 | 13.39 | 14.21 | 13.83 |
| Reinforcement Index, (300%/25%) | 17.4 | 18.55 | 18.70 | 18.15 |
| Reinforcement Index, (300%/100%) | 6.40 | 7.08 | 7.07 | 6.87 |
| Abrasion Loss (DIN) (mm$^3$) | | 93 | 108 | 104 |
| Dynamic Properties, (cured t90 at 149° C.) | | | | |
| Non-linearity (0-10%) 60° C. | | | | |
| G'$_{initial}$ (MPa) | 1.78 | 2.73 | 2.98 | 2.43 |
| ΔG' (MPa) | 0.45 | 1.21 | 1.41 | 1.10 |
| G''$_{max}$ (MPa) | 1.75 | 0.35 | 0.34 | 0.28 |
| tan δ$_{max}$ | 0.11 | 0.15 | 0.15 | 0.16 |
| Temperature Dependence | | | | |
| tan δ 0° C. | 0.63 | 0.57 | 0.48 | 0.44 |
| tan δ 60° C. | 0.10 | 0.14 | 0.14 | 0.15 |
| G' 0° C. (MPa) | 6.27 | 7.22 | 6.12 | 5.38 |
| G' 60° C. (MPa) | 1.60 | 2.00 | 2.02 | 1.81 |

What is claimed is:

1. A mercaptofunctional silane of general Formula (1):

$$[HSG^1SiZ^\theta Z^\beta]_m[HSG^2SiZ^\beta{}_3]_n[HSG^3SiZ^\beta{}_2X]_o$$
$$[[HSG^4SiZ^\beta X_2]_p \quad (1)$$

wherein:
each occurrence of $G^1$, $G^2$, $G^3$, and $G^4$ is independently a hydrocarbylene group containing from 1 to 30 carbon derived by substitution of a hydrogen on alkyl, alkenyl, aryl, or aralkyl or a divalent heterocarbon group containing 2 to 30 carbon atoms and one or more etheric oxygen (—O—) and/or sulfur (—S—) atoms;

each occurrence of X is independently selected from the group consisting of —Cl, —Br, RO—, RC(=O)O—, $R_2C$=NO—, $R_2NO$—, —R, $(HO)_{d-1}G^5O$—, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^5$ is independently a substituted hydrocarbon group from 2 to 15 carbon atoms or a substituted heterocarbon group from about 4 to 15 carbon atoms and contains one or more etheric oxygen atoms;

each occurrence of $Z^\beta$, which forms a bridging structure between two silicon atoms, is $[-OG^5(OH)_{d-2}O-]_{0.5}$, wherein each occurrence of $G^5$ is independently selected from the group consisting of a hydrocarbylene group of from 2 to 15 carbon atoms or a divalent heterocarbon group of from 4 to 15 carbon atoms containing one or more etheric oxygen atoms;

each occurrence of $Z^\theta$, which forms a cyclic structure with a silicon atom, is independently given by $-OG^5(OH)_{d-2}O-$, wherein $G^5$ is independently selected form the group consisting of a hydrocarbylene group of from 2 to 15 carbon atoms or a divalent heterocarbon group of from 4 to 15 carbon atoms containing one or more etheric oxygen atoms;

each occurrence of subscripts d, m, n, o and p independently is an integer wherein d is from 2 to 6 in a first embodiment, 2 or 3 in a second embodiment and 2 in a third embodiment; m is 0 to 20; n is 0 to 18; o is 0 to 20; and, p is 0 to 20; with the proviso that m+n+o+p is equal to or greater than 2.

2. The mercaptofunctional silane of claim 1 wherein:
each occurrence of $G^1$, $G^2$, $G^1$ and $G^4$ is independently a hydrocarbylene group containing from 1 to 30 carbon atoms derived by substitution of a hydrogen on alkyl, alkenyl, aryl, or aralkyl;

each occurrence of $Z^\beta$, which forms a bridging structure between two silicon atoms, is independently [—O$(R^OCR^O)_fO$—$]_{0.5}$, wherein each occurrence of $R^O$ is independently given by one of the members for R, and f is from 2 to 15;

each occurrence of $Z^\theta$, which forms a cyclic structure with a silicon atom, is independently —O$(R^OCR^O)_fO$—, wherein each occurrence of $R^O$ is independently given by one of the members for R, and f is 2 to 15;

each occurrence of X is independently —OR, wherein each occurrence of R is independently selected from the group consisting of straight, cyclic and branched alkyl, alkenyl, aryl and aralkyl containing up to 18 carbon atoms; and, each occurrence of m, n, o, and p independently is an integer wherein m is from 0 to 20, n is specifically from 0 to 18, o is from 0 to 20, and p is from 0 to 20, with the proviso that m+n+o+p is equal to or greater than 2.

3. The mercaptofunctional silane of claim 2 wherein each occurrence of $G^1$, $G^2$, $G^3$ and $G^4$ is independently a straight or branched chain alkylene group of up to 6 carbon atoms; each occurrence of $R^O$ is independently hydrogen or a straight or branched chain alkyl group of up to 6 carbon atoms and f is 2 to 4; and, m is 0 to 5, n is 0 to 4, o is 0 to 5 and p is 0 to 5, with the proviso that m+n+op is equal to or greater than 2.

4. The mercaptofunctional silane of claim 3 wherein each occurrence of $G^1$, $G^2$, $G^3$ and $G^4$ is independently 3 carbon atoms, each occurrence of $R^O$ is independently hydrogen or straight or branched chain alkyl group of 1 to 3 carbon atoms and f is 2 or 3; and, m is 0 or 1, n is 1 or 2, o is 1 or 2 and p is 0 or 1, with the proviso that m+n+op is equal to or greater than 2.

5. The mercaptofunctional silane of claim 1 wherein:
each occurrence of $G^1$, $G^2$, $G^3$ and $G^4$ is independently a group derived by substitution of hydrogen on alkyl, alkenyl, aryl, or aralkyl having up to 30 carbon atoms;

each occurrence of X is independently selected from the group consisting of —Cl, —Br, RO—, RC(=O)O—, $R_2C$=NO—, $R_2NO$—, $R_2N$—, —R, $(HO)_{d-1}G^5O$—, $HO(CR^O{}_2)_fO$—, and $HO(CR^O{}_2CR^O{}_2O)_e$—, wherein each R is independently selected from the group consisting of hydrogen or straight, cyclic or branched alkyl, alkenyl, aryl, and aralkyl groups of up to 18 carbon atoms;

$G^5$ is independently a hydrocarbylene group of from 2 to 15 carbon atoms or a heterocarbylene group of from 4 to 15 carbon atoms containing one or more etheric oxygen atoms;

$R^O$ is independently given by one of the members for R;

each occurrence of $Z^\beta$, which forms a bridging structure between two silicon atoms, is independently selected from the group consisting of, $[-OG^5(OH)_{d-2}O-]_{0.5}$, $[-O(CR^O{}_2CR^O{}_2O)_e-]_{0.5}$ and $[-O(R^OCR^O)_fO-]_{0.5}$, wherein each occurrence of $R^O$ is independently given by one of the members listed for R;

each occurrence of $Z^\theta$, which forms a cyclic structure with a silicon atom, is independently given by $-OG^4(OH)_{d-2}O-$, $-O(CR^O{}_2CR^O{}_2O)_n-$ and $-O(R^OCR^O)_fO-$ wherein each occurrence of $R^O$ is independently given by one of the members for R; and, each occurrence of the subscripts d, e, f, m, n, o and p is independently an integer wherein d is from 2 to 6, e is from 2 to 7, f is from 2 to 15, m is from 0 to 20, n is from 0 to 18, o is from 0 to 20 and, p is from 0 to 20, with the proviso that m+n+o+p is equal to or greater than 2.

6. The mercaptofunctional silane of claim 5 wherein d is 2 to 4, e is 2 to 4, f is 2 to 4, m is 0 to 5, n is 0 to 4, o is 0 to 5 and p is 0 to 5, with the proviso that m+n+op is equal to or greater than 2.

7. The mercaptofunctional silane of claims 6 wherein d is 2, e is 2, f is 3, m is 1 or 2, n is 1 or 2, o is 1 or 2 and p is 0 to 2, with the proviso that m+n+op is equal to or greater than 2.

8. The monofunctional silane of claim 1 which is at least one member selected from the group consisting of 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propane-1-thiol; 3-(2-{3-[2-(3-mercapto-propy)-4,4,6-trimethyl-[1,3,2]dioxasilinan-2-yloxy]-2-methyl-propoxy}-4,4,6-trimethyl-[1,3,2]dioxasilinan-2-yl)-propane-thiol; 3-(2-{3-[2-(3-mercapto-propyl)-4,4,6-trimethyl-[1,3,2]di-oxasilinan-2-yloxy]-1,1-dimethyl-butoxy}-4,4,6-trimethyl-[1,3,2]dioxasilinan-2-yl)-propane-1-thiol; 3-({3-[2-(mer-capto-propyl)-5-methyl-[1,3,2]dioxasilinan-yloxy]2- methyl-propoxy}-bis-[3-hydroxy-2-methyl-propoxy]-silanyl)-propane-1-thiol; 3-[{3-[{3-bis-(3-hydroxy-2-methyl-propyl)-(3-mercapto-propyl)-silanyloxy]-1-methyl-propoxy}-(3-hydroxy-2-methyl-propoxy)-(3-mercapto-propyl)-silanyloxy]-2-methyl-propan-1-ol; 3-[[3-((3-hydroxy-3-methyl-propoxy)-3-mercapto-propyl)-{3-[2-(3-mercapto-propyl)-5-methyl-[1,3,2]dioxasilinan-2-yloxy]-1-methyl-propoxy}-silanyloxy)-2-methyl-propoxy-(3-hydroxy-2-methyl-propoxy)-3-mercapto-propyl)-silanyl]-2-methylpropan-1-ol; 3-(2-{3-[2-(3-mercapato-butyl)-[1,3,2] dioxasilinan-2-yloxy]-propoxy}-[1,3,2]dioxasilinan-2-yl)-butane-1-thiol; 3-(2-{3-[2-(3-mercapto-phenyl)-4,4,6-trimethyl-[1,3,2]dioxasilinan-2-yloxy]-2-methyl-propoxy}-4,4,6-trimethyl-[1,3,2]dioxasilinan-2-yl)-3-benzene-thiol; 3-(2-{3-[2-(3-mercapto-cyclohexyl)-4,4,6-trimethyl-[1,3,2]dioxasilinan-2-yloxy]-1,1-dimethyl-butoxy}-4,4,6-trimethyl-[1,3,2]dioxasilinan-2-yl)-cyclohexane-1-thiol; 3-({3-[2-mercapto-methyl)-5-methyl-[1,3,2]dioxasilinan-2-yloxy]-2-methyl-propoxy}-diethoxy]-silanyl)-methane-1-thiol; 3-[{3-[{3-bis-(3-hydroxy-2,2-dimethyl-propyl}-(3-mercapt-propyl)-silanloxy]-2,2-dimethyl-propoxy)-(3-hydroxy-2,2-dimethyl-propoxy)-(3-mercapto-propyl)-silanyloxy]-2,2-dimethyl-propan-1-ol; 3-[[3-((3-hydroxy-3-phenyl-propoxy)-3-mercapto-propyl)-{3-[2-(3-mercapto-propyl)-5-phenyl-[1,3,2]dioxasilinan-2-yloxy]-2-phenyl-1-propoxy}-silanyloxy)-2-phenyl-propoxy-(3-hydroxy-2-phenyl-propoxy)-3-mercapto-propyl)-silanyl]-2-phenylpropan-1-ol; 3-[{3-[(methyl)-(3-hydroxy-2-methyl-propoxy)-(3-mercapto-propyl)-silanyloxy]-2-methyl-propoxy}-methyl)-(3-mercapto-propyl)-silanyloxy]-2-methyl-propan-1-ol.

9. A process for preparing mercaptofunctional silane which comprises reacting
a) at least one mercaptofunctional silane selected from the group consisting of general Formulae (2), (3), (4) and (5):

  (2)

  (3)

  (4)

  (5)

wherein:
each occurrence of $G^1$, $G^2$, $G^3$, and $G^4$ is independently a hydrocarbylene group containing from 1 to 30 carbon atoms derived by substitution of a hydrogen on alkyl, alkenyl, aryl, or aralkyl or a substituted divalent heterocarbon containing 2 to 30 carbon atoms and one or more etheric oxygen (—O—) and/or sulfur (—S—) atoms;

each occurrence of X is independently selected from the group consisting of —Cl, —Br, RO—, RC(=O)O—, $R_2$C=NO—, $R_2$NO—, —R, wherein each R is independently selected from the group consisting of hydrogen or straight, cyclic or branched alkyl, alkenyl, aryl or aralkyl wherein each of up to 18 carbon atoms, with the proviso that at least one X is a hydrolyzable group, with b) one or more polyhydroxy-containing compounds of general Formula (6):

$G^5(OH)_d$  (6)

wherein $G^5$ is a hydrocarbyl group of from 1 to 15 carbon atoms or a heterocarbyl group of from 4 to 15 carbon atoms containing one or more etheric oxygen atoms and d is an integer of from 2 to 6, under tranesterification reaction conditions, thereby producing mercaptofunctional silane of general Formula (1):

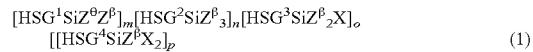  (1)

wherein:
each occurrence of $G^1$, $G^2$, $G^3$, and $G^4$ is independently a hydrocarbylene group containing from 1 to 30 carbon derived by substitution of a hydrogen on alkyl, alkenyl, aryl, or aralkyl or a substituted divalent heterocarbon containing 2 to 30 carbon atoms and one or more etheric oxygen (—O—) and/or sulfur (—S—) atoms;

each occurrence of X is independently selected from the group consisting of —Cl, —Br, RO—, RC(=O)O—, $R_2$C=NO—, $R_2$NO—, —R, $(HO)_{d-1}G^5O$—, wherein each R is independently selected from the group consisting of hydrogen, straight, cyclic or branched alkyl that can or can not contain unsaturation, alkenyl groups, aryl groups, and aralkyl groups, wherein each R, other than hydrogen, contains from 1 to 18 carbon atoms, $G^5$ is independently a hydrocarbylene group of from 2 to 15 carbon atoms or a divalent heterocarbon group of from 4 to 15 carbon atoms containing one or more etheric oxygen atoms;

each occurrence of $Z^\beta$, which forms a bridging structure between two silicon atoms, is $[—OG^5(OH)_{d-2}O—]_{0.5}$, wherein each occurrence of $G^5$ is independently selected from the group consisting of a hydrocarbylene group from 2 to 15 carbon atoms or a divalent heterocarbon group of from 4 to 15 carbon atoms containing one or more etheric oxygen atoms;

each occurrence of $Z^\theta$, which forms a cyclic structure with a silicon atom, is independently given by —$OG^5(OH)_{d-2}O$—, wherein $G^5$ is independently selected form the group consisting of a hydrocarbylene group of from 2 to 15 carbon atoms or a divalent heterocarbon group of from 4 to 15 carbon atoms containing one or more etheric oxygen atoms;

each occurrence of subscripts d, m, n, o and p independently is an integer wherein d is from 2 to 6 in a first embodiment, 2 or 3 in a second embodiment and 2 in a third embodiment; m is 0 to 20; n is 0 to 18; o is 0 to 20; and, p is 0 to 20, with the proviso that m+n+o+p is equal to or greater than 2.

10. The process of claim 9 wherein the mercaptofunctional silane of Formulae (2), (3), (4) and/or (5) is at least one trialkoxysilane selected from the group consisting of general Formulae (7) to (10):

  (7)

  (8)

  (9)

  (10)

wherein:
each occurrence of $G^1$, $G^2$, $G^3$, and $G^4$ is independently a hydrocarbylene group containing from 1 to 12 carbon atoms derived by substitution of a hydrogen on alkyl, alkenyl, aryl, or aralkyl; and,
each R independently has one of the aforestated meanings.

11. The process of claim 10 wherein each R independently is a methyl, ethyl, propyl, isopropyl, n-butyl or sec-butyl group.

12. The process of claim 9 wherein mercaptofunctional silane (1) is a dimer, oligomer or polymer in which each silane unit is bonded to an adjacent silane unit through a bridging group resulting from the reaction of the selected mercaptofunctional silane monomer(s) with one or more polyhydroxy-containing compounds of general Formula (11):

$$G^5(OH)_d \qquad (11)$$

wherein $G^5$ is a hydrocarbyl group of from 2 to 15 carbon atoms or a heterocarbyl group of from 4 to 15 carbon atoms containing one or more etheric oxygen atoms and d is an integer of from 2 to 6.

13. The process of claim 12 wherein polyhydroxy-containing compound (11) is a diol of at least one of general Formulae (12) and (13):

$$HO(R^0CR^0)_fOH \qquad (12)$$

$$HO(CR^0{}_2CR^0{}_2O)_eH \qquad (13)$$

wherein $R^0$ is independently given by one of the members listed above for R, f is 2 to 15 and e is 2 to 7.

14. The process of claim 13 wherein the diol is a least one member selected from the group consisting of $HOCH_2CH_2OH$, $HOCH_2CH_2CH_2OH$, $HOCH_2CH_2CH_2CH_2OH$, $HOCH_2CH(CH_3)CH_2OH$, $(CH_3)_2C(OH)CH_2CH(OH)CH_3$, $CH_3CH(OH)CH_2CH_2OH$, $HOCH_2CH_2OCH_2CH_2OH$, $HOCH_2CH_2CH_2OCH_2CH_2CH_2OH$, $HOCH_2CH(CH_3)OCH_2CH(CH_3)OH$, $HOCH_2CH_2OCH_2CH_2OCH_2CH_2OH$, a diol of Formula (11) or a adiol of Formula (12) wherein $R^0$ is hydrogen or methyl and e is 3 to 7.

15. The process of claim 12 wherein polyhydroxy-containing compound (11) conforms to Formula (14):

$$G^5(OH)_d \qquad (14)$$

wherein $G^5$ is a is a substituted hydrocarbyl group of from 2 to 15 carbon atoms or a substituted heterocarbon of from 4 to 15 carbon atoms containing one or more etheric oxygen atoms; and, d is an integer of from 3 to 6.

16. The process of claim 15 wherein polyhydroxy-containing compound (14) is at least one member selected from the group consisting of glycerol, trimethylolethane, trimethylolpropane, 1,2,4-butanetriol, 1,2,6-hexanetriol, pentaerythritol, dipentaerythritol, tripentaerythritol, mannitol, galacticol and sorbitol.

17. The process of claim 9 wherein product mercaptofunctional silane (1) is at least one member selected from the group consisting of 3-(2-{3-[2-(3-mercapto-propyl)-5-methyl-[1,3,2]dioxasilinan-2-yloxy]-2-methyl-propoxy}-5-methyl-[1,3,2]dioxasilinan-2-yl)-propane-1-thiol; 3-(2-{3-[2-(3-mercapto-propy)-4,4,6-trimethyl-[1,3,2]dioxasilinan-2-yloxy]-2-methyl-propoxy}-4,4,6-trimethyl-[1,3,2]dioxasilinan-2-yl)-propane-thiol; 3-(2-{3-[2-(3-mercapto-propyl)-4,4,6-trimethyl-[1,3,2]dioxasilinan-2-yloxy]-1,1-dimethyl-butoxy}-4,4,6-trimethyl-[1,3,2]dioxasilinan-2-yl)-propane-1-thiol; 3-({3-[2-mercapto-propyl)-5-methyl-[1,3,2]dioxasilinan-yloxy]-2-methyl-propoxy}-bis-[3-hydroxy-2-methyl-propoxy]-silanyl)-propane-1-thiol; 3-[{3-[{3-bis-(3-hydroxy-2-methyl-propyl)-(3-mercapto-propyl)-silanyloxy]-1-methyl-propoxy}-(3-hydroxy-2-methyl-propoxy)-(3-mercapto-propyl)-silanyloxy]-2-methyl-propan-1-ol; 3-[[3-((3-hydroxy-3-methyl-propoxy)-3-mercapto-propyl)-{3-[2-(3-mercapto-propyl)-5-methyl-[1,3,2]dioxasilinan-2-yloxy]-1-methyl-propoxy}-silanyloxy)-2-methyl-propoxy-(3-hydroxy-2-methyl-propoxy)-3-mercapto-propyl)-silanyl]-2-methylpropan-1-ol; 3-(2-{3-[2-(3-mercapto-butyl)-[1,3,2]dioxasilinan-2-yloxy]-propoxy}-[1,3,2]dioxasilinan-2-yl)-butane-1-thiol; 3-(2-{3-[2-(3-mercapto-phenyl)-4,4,6-trimethyl-[1,3,2]dioxasilinan-2-yloxy]-2-methyl-propoxy}-4,4,6-trimethyl-[1,3,2]dioxasilinan-2-yl)-3-benzene-thiol; 3-(2-{3-[2-(3-mercapto-cyclohexyl)-4,4,6-trimethyl-[1,3,2]dioxasilinan-2-yloxy]-1,1-dimethyl-butoxy}-4,4,6-trimethyl-[1,3,2]dioxasilinan-2-yl)-cyclohexane-1-thiol; 3-({3-[2-mercapto-methyl)-5-methyl-[1,3,2]dioxasilinan-2-yloxy]-2-methyl-propoxy}-diethoxy]-silanyl)-methane-1-thiol; 3-[3-[{3-bis-(3-hydroxy-2,2-dimethyl-propyl)-(3-mercapt-propyl)-silanyloxy]-2,2-dimethyl-propoxy}-(3-hydroxy-2,2-dimethyl-propoxy)-(3-mercapto-propyl)-silanyloxy]-2,2-dimethyl-propan-1-ol; 3-[[3-((3-hydroxy-3-phenyl-propoxy)-3-mercapto-propyl)-{3-[2-(3-mercapto-propyl)-5-phenyl-[1,3,2]dioxasilinan-2-yloxy]-2-phenyl-1-propoxy}-silanyloxy)-2-phenyl-propoxy-(3-hydroxy-2-phenyl-propoxy)-3-mercapto-propyl)-silanyl]-2-phenylpropan-1-ol; and, 3-[{3-[(methyl)-(3-hydroxy-2-methyl-propoxy)-(3-mercapto-propyl)-silanyloxy]-2-methyl-propoxy}-methyl)-(3-mercapto-propyl)-silanyloxy]-2-methyl-propan-1-ol.

18. Free-flowing particulate treated with at least one mercaptofunctional silane of Formula (1) of claim 1, the silane being present in admixture with and/or chemically bonded to particulate.

19. The free-flowing particulate of claim 18 wherein the particulate is at least one member selected from the group consisting of metal oxide, siliceous material and carbon black.

20. The free-flowing particulate of claim 19 wherein the metal oxide is at least one member selected from the group consisting of silica, titanium and alumina; and, the siliceous material is at least one member of the group consisting of aluminosilicate, clay and talc.

21. The free-flowing particulate of claim 19 wherein the particulate is at least one member selected from the group consisting of mixtures of silica and carbon black and mixtures of silica and alumina.

* * * * *